(12) United States Patent
Leonardi et al.

(10) Patent No.: US 11,471,518 B2
(45) Date of Patent: *Oct. 18, 2022

(54) FUSION PROTEINS COMPRISING MODIFIED ALPHA VIRUS SURFACE GLYCOPROTEINS AND TUMOR ASSOCIATED ANTIGEN AND METHODS THEREOF

(71) Applicant: OMNICYTE, New York, NY (US)

(72) Inventors: Peter Leonardi, New York, NY (US); Elin Martina Pola, Agunnaryd (SE); Jeffrey Babad, Mamaroneck, NY (US)

(73) Assignee: OMNICYTE, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/844,271

(22) Filed: Apr. 9, 2020

(65) Prior Publication Data

US 2021/0077600 A1 Mar. 18, 2021

Related U.S. Application Data

(63) Continuation of application No. 15/558,918, filed as application No. PCT/US2016/002320 on Mar. 18, 2016, now Pat. No. 10,660,948.

(Continued)

(51) Int. Cl.
*C12N 7/00* (2006.01)
*A61K 39/00* (2006.01)
(Continued)

(52) U.S. Cl.
CPC .. *A61K 39/0011* (2013.01); *A61K 39/001188* (2018.08); *A61K 39/385* (2013.01);
(Continued)

(58) Field of Classification Search
None
See application file for complete search history.

(56) References Cited

U.S. PATENT DOCUMENTS

| 5,726,288 A | 3/1998 | Call et al. |
| 6,004,557 A | 12/1999 | Edwards et al. |

(Continued)

FOREIGN PATENT DOCUMENTS

| CN | 1691964 A | 11/2005 |
| RU | 2395519 C2 | 7/2010 |

(Continued)

OTHER PUBLICATIONS

An et al., "Determination of Glycosylation Sites and Site-specific heterogeneity in Glycoproteins," Curr Opin Chem Biol 13(4): 421-426 (Year: 2009).*

(Continued)

*Primary Examiner* — M Franco G Salvoza
(74) *Attorney, Agent, or Firm* — Leason Ellis LLP

(57) ABSTRACT

The present disclosure relates to fusion proteins that comprise one or more modified alpha virus surface glycoproteins and one or more tumor specific antigens. Also disclosed are fusion proteins that comprise one or more modified alpha virus surface glycoproteins and one or more viral specific antigens. Also disclosed are fusion proteins that comprise one or more modified alpha virus surface glycoproteins. It also relates to methods to activate the immune system in cancer patients to infiltrate and kill tumor cells or cells infected with a latent virus. The present disclosure provides a platform technology that elicits a faster, broader and stronger immune response using the fusion proteins.

10 Claims, 15 Drawing Sheets

Figure 1A:
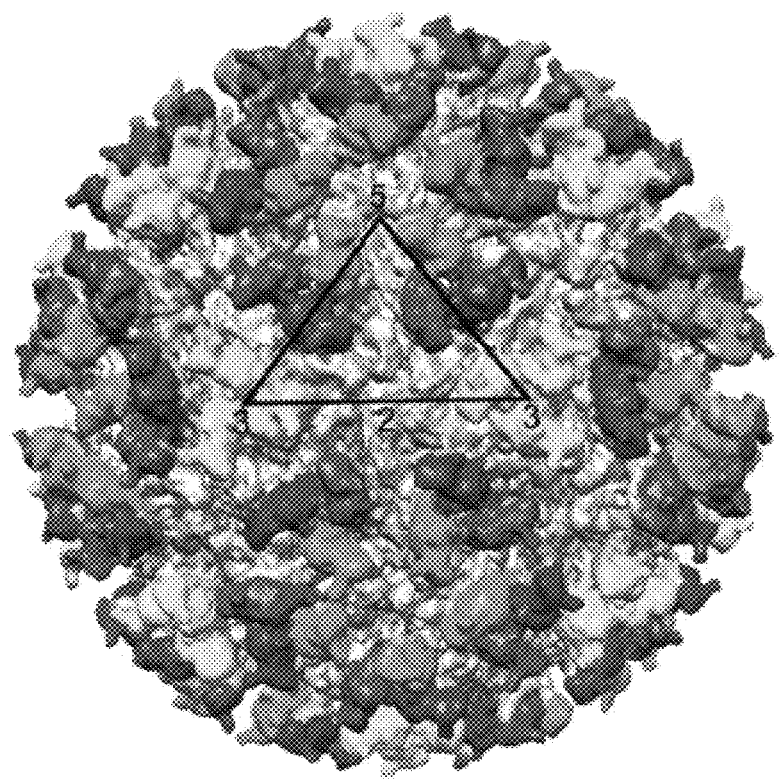

Specification includes a Sequence Listing.

Related U.S. Application Data

(60) Provisional application No. 62/134,933, filed on Mar. 18, 2015.

(51) Int. Cl.
    *C07K 14/005*     (2006.01)
    *A61K 39/385*     (2006.01)
    *A61P 35/00*     (2006.01)

(52) U.S. Cl.
    CPC .............. *A61P 35/00* (2018.01); *C07K 14/005* (2013.01); *A61K 2039/6075* (2013.01); *C07K 2319/00* (2013.01); *C12N 2770/36134* (2013.01)

(56) References Cited

U.S. PATENT DOCUMENTS

| | | | |
|---|---|---|---|
| 6,168,932 | B1 | 1/2001 | Uckun et al. |
| 6,992,174 | B2 * | 1/2006 | Gillies ................... A61P 3/04 |
| | | | 530/387.3 |
| 2004/0180354 | A1 | 9/2004 | Simard et al. |
| 2005/0130259 | A1 | 6/2005 | Ideno et al. |
| 2008/0260775 | A1 | 10/2008 | Johnston et al. |
| 2009/0075388 | A1 | 3/2009 | Moore et al. |
| 2012/0328655 | A1 | 12/2012 | Dubensky, Jr. et al. |
| 2015/0017194 | A1 | 1/2015 | Akahata et al. |

FOREIGN PATENT DOCUMENTS

| | | |
|---|---|---|
| RU | 2012107671 A | 9/2013 |
| WO | 2011011584 A1 | 1/2011 |
| WO | 2012112691 A1 | 9/2012 |

OTHER PUBLICATIONS

Spiro, "Protein glycosylation: nature, distribution, enzymatic formation, and disease implications of glycopeptide bonds," Glycobiology, vol. 12, No. 4: 43R-56R (Year: 2002).*

Cheever et al., "The Prioritization of Cancer Antigens: A National Cancer Institute Pilot Project for the Acceleration of Translational Research," Clin Cancer Res. 15(17): 5323-5337 (Year: 2009).*

Cheever, Martin A., et al. "The prioritization of cancer antigens: a national cancer institute pilot project for the acceleration of translational research." Clinical cancer research 15.17 (2009): 5323-5337.

Frolov, Ilya, et al. "Alphavirus-based expression vectors: strategies and applications." Proceedings of the National Academy of Sciences 93.21 (1996): 11371-11377.

International Search Report and Written Opinion in corresponding PCT Application No. PCT/US2016/023203, dated Oct. 31, 2016.

Ebner et al. "Identification of multiple T cell epitopes on Bet v I, the major birch pollen allergen, using specific T cell clones and overlapping peptides." The Journal of Immunology 150.3 (1993): 1047-1054.

Extended European Search Report and Written Opinion in corresponding European Application EP16765844, dated Oct. 11, 2018.

European Examination Report in corresponding European Application 16765844.2 dated Jan. 21, 2020. 6 pages.

Frankel et al. "Characterization of diphtheria fusion proteins targeted to the human interleukin-3 receptor." Protein Engineering 13.8 (2000): 575-581.

Japanese Office Action in corresponding Japanese Patent Application No. 2018-500274 dated Jan. 28, 2020. 10 pages.

Mendoza, Querubin P., Jeff Stanley, and Diane E. Griffin. "Monoclonal antibodies to the E1 and E2 glycoproteins of Sindbis virus: definition of epitopes and efficiency of protection from fatal encephalitis." Journal of general virology 69.12 (1988): 3015-3022.

Pakula et al. "Genetic analysis of protein stability and function." Annual Review of Genetics 23.1 (1989): 289-310.

Brazilian Office Action in corresponding Brazilian Patent Application No. 112017019776-6 dated Jan. 1, 2020 (an English machine translation attached hereto). 6 pages.

Russian Office Action in corresponding Russian Patent Application No. 2017132190 dated Aug. 29, 2019 (an English machine translation attached hereto).. 11 pages.

Russian Office Action in corresponding Russian Patent Application No. 2017132190 dated Jan. 23, 2020 (an English machine translation attached hereto).. 8 pages.

Tokuriki et al. "Stability effects of mutations and protein evolvability." Current Opinion in Structural Biology 19.5 (2009): 596-604.

Chinese Office Action in Corresponding Chinese Patent Application No. 201680022074.2 dated Jul. 27, 2020. 13 pages.

\* cited by examiner

Amino acid sequence:

E3-E2-link-E1-TEV-link-NY-ESO-1-6X His:

| | |
|---|---:|
| MSAAPLVTAMCLLGNVSFPCDRPPTCYTREPSRALDILEENVNHEAYDTL | 50 |
| LNAILRCGSSGRSKRSVIDDFTLTSPYLGTCSYCHHTVPCFSPVKIEQVW | 100 |
| DEADDNTIRIQTSAQFGYDQSGAASANKYRYMSLKQDHTVKEGTMDDIKI | 150 |
| STSGPCRRLSYKGYFLLAKCPPGDSVTVSIVSSNSATSCTLARKIKPKFV | 200 |
| GREKYDLPPVHGKKIPCTVYDRLKETTAGYITMHRPRPHAYTSYLEESSG | 250 |
| KVYAKPPSGKNITYECKCGDYKTGTVSTRTEITGCTAIKQCVAYKSDQTK | 300 |
| WVFNSPDLIRHDDHTAQGKLHLPFKLIPSTCMVPVAHAPNVIHGFKHISL | 350 |
| QLDTDHLTLLTTRRLGANPEPTTEWIVGKTVRNFTVDRDGLEYIWGNHEP | 400 |
| VRVYAQESAPGDPHGWPHEIVQHYYHRHPGGGGSGGGGSGGGGSGGGGYE | 450 |
| HATTVPNVPQIPYKALVERAGYAPLNLEITVMSSEVLPSTNQEYITCKFT | 500 |
| TVVPSPKIKCCGSLECQPAAHADYTCKVFGGVYPFMWGGAQCFCDSENSQ | 550 |
| MSEAYVELSADCASDHAQAIKVHTAAMKVGLRIVYGNTTSFLDVYVNGVT | 600 |
| PGTSKDLKVIAGPISASFTPFDHKVVIHRGLVYNYDFPEYGAMKPGAFGD | 650 |
| IQATSLTSKDLIASTDIRLLKPSAKNVHVPYTQASSGFEMWKNNSGRPLQ | 700 |
| ETAPFGCKIAVNPLRAVDCSYGNIPISIDIPNAAFIRTSDAPLVSTVKCE | 750 |
| VSECTYSADFGGMATLQYVSDREGQCPVHSHSSTATLQESTVHVLEKGAV | 800 |
| TVHFSTASPQANFIVSLCGKKTTCNAECKPPADHIVSTPHKNDQEFQAA | 850 |
| ISKTSENLYFQGGGGGSGGGGSGGGGSGARGPESRLLEFYLAMPFATPMEA | 900 |
| ELARRSLAQDAPPLPVPGVLLKEFTVSGNILTIRLTAADHRQLQLSISSC | 950 |
| LQQLSLLMWITQCFLPVFLAQPPSGQRRHHHHHH | 984 |

SEQ ID NO: 1

BOLD N = glycosylation sites

FIG. 5

DNA sequence of Construct:

```
      ATGTCAGCCG CTCCACTCGT CACTGCTATG TGCCTGCTCG GTAACGTCAG CTTCCCTTGC
  61  GACAGACCCC CAACTTGCTA CACTCGTGAG CCATCTAGGG CTCTCGATAT CTTGGAGGAA
 121  AACGTGAACC ACGAGGCTTA CGACACCCTG CTCAACGCCA TCCTGAGATG CGGATCCAGC
 181  GGTCGCTCCA AGCGTAGCGT GATTGACGAT TTCACACTCA CGTCGCCTTA CTTGGGTACC
 241  TGCTCCTACT GTCACCATAC TGTCCCGTGT TTCTCACCTG TCAAGATCGA GCAGGTTTGG
 301  GACGAAGCAG ACGATAACAC AATCCGCATT CAGACGAGCG CTCAATTCGG TTACGATCAG
 361  AGCGGCGCTG CCTCTGCTAA CAAATACCGT TACATGTCTC TCAAACAAGA CCACACCGTC
 421  AAGGAGGGCA CTATGGACGA TATCAAGATT CTACTTCAG GACCTTGCCG CCGTCTGTCT
 481  TACAAAGGTT ACTTCTTGCT GGCTAAGTGT CCTCCCGGAG ACTCAGTCAC AGTTAGTATC
 541  GTCTCTTCAA ACTCTGCAAC ATCATGCACG CTGGCGCGCA AGATTAAACC AAAGTTCGTT
 601  GGCCGTGAGA AATACGACCT CCCACCGGTG CACGGAAAGA AATCCCTTG TACCGTCTAC
 661  GATCGTTTGA AGGAAACCAC TGCCGGCTAC ATTACCATGC ACAGGCCAAG ACCGCATGCT
 721  TACACTAGTT ACCTGGAAGA AAGTTCGGGC AAAGTGTACG CCAAGCCTCC CTCGGGAAAG
 781  AACATCACAT ACGAGTGCAA ATGTGGAGAC TACAAGACCG GTACTGTCAG CACAAGGACG
 841  GAAATCACCG GTTGCACTGC TATTAAGCAG TGTGTCGCCT ACAAATCGGA CCAAACTAAG
 901  TGGGTTTTCA ACTCCCCCGA TCTGATCAGA CACGACGATC ATACTGCCCA GGGAAAATTG
 961  CACCTGCCGT TCAAGCTCAT TCCTTCAACA TGCATGGTGC CCGTCGCTCA TGCCCCAAAC
1021  GTGATCCACG GTTTCAAGCA TATTAGTCTC CAATTGGACA CAGATCACCT CACGCTCTTG
1081  ACAACGAGGA GATTGGGAGC TAACCCTGAG CCCACCACTG AATGGATCGT GGGCAAGACA
1141  GTCCGCAACT TCACGGTGGA CCGTGATGGC CTGGAGTACA TCTGGGGAAA CCACGAACCA
1201  GTTCGCGTGT ACGCTCAGGA GTCCGCACCA GGAGACCCAC ACGGTTGGCC ACATGAAATC
1261  GTCCAACATT ACTACCACCG TCATCCTGGT GGAGGAGGTT CGGGAGGAGG TGGATCCGGA
1321  GGTGGCGGAA GCGGTGGCGG AGGTTACGAG CACGCTACAA CGGTGCCTAA CGTCCCCCAG
1381  ATCCCATACA AGGCCTTGGT GGAAAGAGCT GGATACGCAC CACTGAACCT CGAGATCACC
1441  GTGATGTCCA GCGAAGTCCT GCCAAGCACA AACCAGGAGT ACATCACGTG CAAGTTCACC
1501  ACTGTGGTCC ATCACCGAA AATTAAGTGC TGTGGTAGTC TGGAATGCCA ACCTGCAGCG
1561  CACGCTGACT ACACTTGTAA GGTTTTCGGC GGAGTGTACC CCTTCATGTG GGGTGGCGCT
1621  CAGTGCTTCT GTGACAGTGA GAACTCGCAA ATGTCCGAGG CTTACGTTGA ACTGTCTGCA
1681  GACTGCGCGT CAGATCACGC ACAGGCGATC AAAGTGCATA CCGCTGCCAT GAAGGTTGGT
1741  TTGCGCATTG TGTACGGCAA CACAACGTCT TTCCTGGATG TCTACGTTAA CGGCGTGACA
1801  CCTGAACGT CAAAAGACCT GAAGGTCATC GCAGGCCCGA TTAGTGCGTC GTTCACTCCT
1861  TTCGATCACA AGGTTGTGAT CCATAGGCGT CTCGTGTACA ACTACGACTT CCCCGAATAC
1921  GGCGCTATGA AACCAGGCGC CTTCGGAGAT ATCCAAGCAA CCAGCCTGAC TTCTAAGGAC
1981  CTCATCGCGA GCACAGATAT TCGTCTGCTC AAACCGTCTG CTAAGAACGT GCACGTCCCC
2041  TACACCCAGG CCTCTTCAGG TTTCGAGATG TGGAAAAACA ACTCCGGCAG CGGCTCCAA
2101  GAAACCGCTC CTTTCGGCTG CAAGATCGCA GTCAACCCCT TGAGAGCGGT TGACTGTAGC
2161  TACGGAAACA TCCCCATTTC TATCGATATT CCAAACGCAG CGTTCATCCG CACATCAGAC
2221  GCCCCACTCG TTAGTACGGT GAAGTGCCAG GTCAGTGAAT GTACATACTC GGCTGATTTC
2281  GGTGGTATGG CCACGTTGCA GTACGTTTCG GACCGTGAGG GTCAATGCCC TGTGCACTCC
2341  CATAGTTCGA CCGCCACTCT GCAGGAGAGC ACCGTTCACG TGCTCGAAAA GGGTGCTGTC
2401  ACCGTTCATT TCTCAACTGC AAGTCCTCAA GCGAACTTCA TCGTGTCTCT CTGCGGCAAG
2461  AAAACCACTT GCAACGCAGA GTGTAAGCCA CCGGCGGACC ACATCGTCTC AACCCCCCAT
2521  AAAAACGATC AGGAGTTCCA AGCTGCCATT TCGAAGACTT CCGAAAACCT GTACTTCCAG
2581  GGAGGAGGTG GAGGATCCGG TGGAGGAGGT AGCGGAGGAG GTGGATCTGG TGCTAGGGGA
2641  CCAGAGTCCA GATTGCTGGA GTTCTACTTG GCTATGCCCT TCGCCACCCC AATGGAGGCT
2701  GAATTGGCAA GACGTTCCCT GGCACAAGAC GCACCTCCAC TGCCTGTCCC GGAGTTCTC
2761  TTGAAGGAGT TCACTGTGAG CGGTAACATC TTGACCATTA GGCTGACTGC AGCGGACCAC
2821  AGACAGTTGC AACTGTCAAT CTCCAGCTGC CTGCAGCAAC TCAGTCTGCT CATGTGGATT
2881  ACCCAGTGTT TCTTGCCAGT TTTCCTCGCT CAACCCCCCT CGGGACAGAG AAGACACCAT
2941  CATCATCATC AT
```

SEQ ID NO: 2

```
MGSDVRDLNA LLPAVPSLGG GGGCALPVSG AAQWAPVLDF APPGASAYGS
LGGPAPPPAP PPPPPPPPHS FIKQEPSWGG AEPHEEQCLS AFTVHFSGQF
TGTAGACRYG PFGPPPPSQA SSGQARMFPN APYLPSCLES QPAIRNQGYS
TVTFDGTPSY GHTPSHHAAQ FPNHSFKHED PMGQQGSLGE QQYSVPPPVY
GCHTPTDSCT GSQALLLRTP YSSDNLYQMT SQLECMTWNQ MNLGATLKGV
AAGSSSSVKW TEGQSNHSTG YESDNHTTPI LCGAQYRIHT HGVFRGIQDV
RRVPGVAPTL VRSASETSEK RPFMCAYPGC NKRYFKLSHL QMHSRKHTGE
KPYQCDFKDC ERRFSRSDQL KRHQRRHTGV KPFQCKTCQR KFSRSDHLKT
HTRTHTGKTS EKPFSCRWPS CQKKFARSDE LVRHHNMHQR NMTKLQLAL
```

SEQ ID NO: 3

FIG. 8B- MUC1 (P15941)

```
MTPGTQSPFF LLLLLTVLTV VTGSGHASST PGGEKETSAT QRSSVPSSTE
KNAVSMTSSV LSSHSPGSGS STTQGQDVTL APATEPASGS AATWGQDVTS
VPVTRPALGS TTPPAHDVTS APDNKPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDNRPALGS
TAPPVHNVTS ASGSASGSAS TLVHNGTSAR ATTTPASKST PFSIPSHHSD
TPTTLASHST KTDASSTHHS SVPPLTSSNH STSPQLSTGV SFFFLSFHIS
NLQFNSSLED PSTDYYQELQ RDISEMFLQI YKQGGFLGLS NIKFRPGSVV
VQLTLAFREG TINVHDVETQ FNQYKTEAAS RYNLTISDVS VSDVPFPFSA
QSGAGVPGWG IALLVLVCVL VALAIVYLIA LAVCQCRRKN YGQLDIFPAR
DTYHPMSEYP TYHTHGRYVP PSSTDRSPYE KVSAGNGGSS LSYTNPAVAA
TSANL     ---SEQ ID NO: 4
```

FIG. 8C

LMP2 (P13285)

```
MGSLEMVPMG AGPPSPGGDP DGYDGGNNSQ YPSASGSSGN TPTPPNDEER

ESNEEPPPPY EDPYWGNGDR HSDYQPLGTQ DQSLYLGLQH DGNDGLPPPP

YSPRDDSSQH IYEEAGRGSM NPVCLPVIVA PYLFWLAAIA ASCFTASVST

VVTATGLALS LLLLAAVASS YAAAQRKLLT PVTVLTAVVT FFAICLTWRI

EDPPFNSLLF ALLAAAGGLQ GIYVLVMLVL LILAYRRRWR RLTVCGGIMF

LACVLVLIVD AVLQLSPLLG AVTVVSMTLL LLAFVLWLSS PGGLGTLGAA

LLTLAAALAL LASLILGTLN LTTMPLLMLL WTLVVLLICS SCSSCPLSKI

LLARLFLYAL ALLLLASALI AGGSILQTNF KSLSSTEFIP NLFCMLLLIV

AGILFILAIL TEWGSGNRTY GPVPMCLGGL LTMVAGAVWL TVMSNTLLSA

WILTAGFLIF LIGFALFGVI RCCRYCCYYC LTLESEERPP TPYRNTV --SEQ ID NO: 5
```

FIG. 8D

HPV (E6-P03126 and E7-P03129)

```
E6: MHQKRTAMFQ DPQERPRKLP QLCTELQTTI HDIILECVYC KQQLLRREVY
DFAFRDLCIV YRDGNPYAVC DKCLKFYSKI SEYRHYCYSL YGTTLEQQYN
KPLCDLLIRC INCQKPLCPE EKQRHLDKKQ RFHNIRGRWT GRCMSCCRSS
RTRRETQL----SEQ ID NO: 6
E7: MHGDTPTLHE YMLDLQPETT DLYCYEQLND SSEEEDEIDG PAGQAEPDRA
HYNIVTFCCK CDSTLRLCVQ STHVDIRTLE DLLMGTLGIV CPICSQKP -SEQ ID NO:7
```

HPV 18 (E6-P06463 and E7-P06788)

E6: MARFEDPTRR PYKLPDLCTE LNTSLQDIEI TCVYCKTVLE LTEVFEFAFK DLFVVYRDSI
PHAACHKCID FYSRIRELRH YSDSVYGDTL EKLTNTGLYN LLIRCLRCQK PLNPAEKLRH
LNEKRRFHNI AGHYRGQCHS CCNRARQERL --SEQ ID NO: 8

E7: MHGPKATLQD IVLHLEPQNE IPVDLLCHEQ LSDSEEENDE IDGVNHQHLP
ARRAEPQRHT MLCMCCKCEA RIKLVVESSA DDLRAFQQLF LNTLSFVCPW CASQQ

--SEQ ID NO:9

FIG. 8E

RGL4 (Q8IZJ4)

```
MRKLLTNLPA AAVLSAQVYS AVLQGLWEEN VCGTPGRTRV CTALLYGQVC
    60         70         80         90         100
PFQDSTDGLR TITSILFNWP PENTSVYYQP PQRSSFRIKL AFRNLSWPGL
    110        120        130        140        150
GLEDHQEIVL GQLVLPEPNE AKPDDPAPRP GQHALTMPAL EPAPPLLADL
    160        170        180        190        200
GPALEPESPA ALGPPGYLHS APGPAPAPGE GPPPGTVLEP QSAPESSCPC
    210        220        230        240        250
RGSVKNQPSE ELPDMTTFPP RLLAEQLTLM DAELFKKVVL HECLGCIWGQ
    260        270        280        290        300
GHLKGNEHMA PTVRATIAHF NRLTNCITTS CLGDHSMRAR DRARVVEHWI
    310        320        330        340        350
KVARECLSLN NFSSVHVIVS ALCSNPIGQL HKTWAGVSSK SMKELKELCK
    360        370        380        390        400
KDTAVKRDLL IKAGSFKVAT QERNPQRVQM RLRRQKKGVV PFLGDFLTEL
    410        420        430        440        450
QRLDSAIPDD LDGNTNKRSK EVRVLQEMQL LQVAAMNYRL RPLEKFVTYF
    460        470
IRMEQLSDKE SYKLSCQLEP ENP       SEQ ID NO: 10
```

Amino acid sequence of NY-ESO-1 (P78358)

MQAEGRGTGG STGDADGPGG PGIPDGPGGN AGGPGEAGAT GGRGPRGAGA
ARASGPGGGA PRGPHGGAAS GLNGCCRCGA RGPESRLLEF YLAMPFATPM
EAELARRSLA QDAPPLPVPG VLLKEFTVSG NILTIRLTAA DHRQLQLSIS
SCLQQLSLLM WITQCFLPVF LAQPPSGQRR  -SEQ ID NO:11

FIG. 8F

Full Sindbis structural protein sequence (Capsid, E3, E2 Ectodomain, E2 Transmembrane Domain, 6K, E1 Ectodomain, E1 Transmembrane Domain):

MNRGFFNMLG RRPFPAPTAM WRPRRRRQAA PMPARNGLAS QIQQLTTAVS
ALVIGQATRP QPPRPRPPPR QKKQAPKQPP KPKKPKTQEK KKKQPAKPKP
GKRQRMALKL EADRLFDVKN EDGDVIGHAL AMEGKVMKPL HVKGTIDHPV
LSKLKFTKSS AYDMEFAQLP VNMRSEAFTY TSEHPEGFYN WHHGAVQYSG
GRFTIPRGVG GRGDSGRPIM DNSGRVVAIV LGGADEGTRT ALSVVTWNSK
GKTIKTTPEG TEEWSAAPLV TAMCLLGNVS FPCDRPPTCY TREPSRALDI
LEENVNHEAY DTLLNAILRC GSSGRSKRSV IDDFTLTSPY LGTCSYCHHT
VPCFSPVKIE QVWDEADDNT IRIQTSAQFG YDQSGAASAN KYRYMSLKQD
HTVKEGTMDD IKISTSGPCR RLSYKGYFLL AKCPPGDSVT VSIVSSNSAT
SCTLARKIKP KFVGREKYDL PPVHGKKIPC TVYDRLKETT AGYITMHRPR
PHAYTSYLEE SSGKVYAKPP SGKNITYECK CGDYKTGTVS TRTEITGCTA
IKQCVAYKSD QTKWVFNSPD LIRHDDHTAQ GKLHLPFKLI PSTCMVPVAH
APNVIHGFKH ISLQLDTDHL TLLTTRRLGA NPEPTTEWIV GKTVRNFTVD
RDGLEYIWGN HEPVRVYAQE SAPGDPHGWP HEIVQHYYHR HPVYTILAVA
SATVAMMIGV TVAVLCACKA RRECLTPYAL APNAVIPTSL ALLCCVRSAN
AETFTETMSY LWSNSQPFFW VQLCIPLAAF IVLMRCCSCC LPFLVVAGAY
LAKVDAYEHA TTVPNVPQIP YKALVERAGY APLNLEITVM SSEVLPSTNQ
EYITCKFTTV VPSPKIKCCG SLECQPAAHA DYTCKVFGGV YPFMWGGAQC
FCDSENSQMS EAYVELSADC ASDHAQAIKV HTAAMKVGLR IVYGNTTSFL
DVYVNGVTPG TSKDLKVIAG PISASFTPFD HKVVIHRGLV YNYDFPEYGA
MKPGAFGDIQ ATSLTSKDLI ASTDIRLLKP SAKNVHVPYT QASSGFEMWK
NNSGRPLQET APFGCKIAVN PLRAVDCSYG NIPISIDIPN AAFIRTSDAP
LVSTVKCEVS ECTYSADFGG MATLQYVSDR EGQCPVHSHS STATLQESTV
HVLEKGAVTV HFSTASPQAN FIVSLCGKKT TCNAECKPPA DHIVSTPHKN
DQEFQAAISK TSWSWLFALF GGASSLLIIG LMIFACSMML TSTRR

SEQ ID NO:12

FIG. 9

FUSION PROTEINS COMPRISING MODIFIED ALPHA VIRUS SURFACE GLYCOPROTEINS AND TUMOR ASSOCIATED ANTIGEN AND METHODS THEREOF

CROSS-REFERENCE TO RELATED PATENT APPLICATIONS

This application is a continuation of U.S. patent Application Ser. No. 15/558,918, filed on Sep. 15, 2017, which was a U.S. National Stage Application under 35 U.S.C. § 371 of International Patent Application No. PCT/US2016/023203, filed Mar. 18, 2016, which claims the benefit of U.S. application Ser. No. 62/134,933, filed Mar. 18, 2015, all of which are incorporated by reference in their entireties.

SEQUENCE LISTING

A sequence listing, created on Sep. 11, 2017 as the ASCII text file "10315_004071_US1_SEQLIST.txt" having a file size of 54.6 kilobytes, is incorporated herein by reference in its entirety.

1. FIELD

The present disclosure relates to fusion proteins that comprise one or more modified alpha virus surface glycoproteins and one or more tumor specific antigens. Also disclosed are fusion proteins that comprise one or more modified alpha virus surface glycoproteins and one or more viral specific antigens. Also disclosed are fusion proteins that comprise one or more modified alpha virus surface glycoproteins. It also relates to methods to activate the immune system in cancer patients to infiltrate and kill tumor cells or cells infected with a latent virus. The present disclosure provides a platform technology that elicits a faster, broader and stronger immune response using the fusion proteins.

2. BACKGROUND

Ovarian cancer is the leading cause of death from gynecological malignancy in the US (1). Unfortunately, most cases are not diagnosed until the disease has progressed to stage III or IV, at which point recurrence is common even after an initially successful response to surgery and chemotherapy (2). It has been shown, however, that patients whose tumors are infiltrated with lymphocytes have a significantly higher 5-year survival rate than those who do not (3), suggesting the immune system plays an important role in combatting tumor growth and that immunotherapy could be a successful strategy for fighting this disease. It is also known that many cancers are caused by viral infections.

The immune system plays an important role in controlling and preventing the growth of aberrant tumor cells via a mechanism known as "cancer immunoediting" (4). Cytotoxic CD8 T cells and natural killer (NK) cells can recognize and destroy these cells as they arise. It has been shown that immunodeficient mice lacking these cell types have increased susceptibility to tumor formation (4). However, tumor cells can develop mutations that help them evade detection by the immune system and mature tumors are therefore often poorly immunogenic, which has hindered the successful translation of many of these therapies to human patients (4). Additionally, tumors can form a unique microenvironment that shields them from direct contact with lymphocytes.

However, some advances have been made that are able to circumvent the tumor's immunosuppressive nature. The immunotherapeutic antibodies Ipilimumab and Nivolumab have recently been approved for the treatment of certain cancers. These checkpoint inhibitors target and block the activity of the immunosuppressive receptors CTLA-4 (Ipilimumab) and PD-1 (Nivolumab) on T cells. These drugs are not without safety concerns however, as these immune suppressive mechanisms are important for controlling potentially dangerous autoimmune and allergic reactions. Chimeric antigen receptor (CAR) T cell therapy has shown strong potential for treating blood-based cancers such as B cell acute lymphoblastic leukemia (ALL). To generate CAR T cells, the patient's own T cells are harvested and genetically modified to express a receptor that will recognize a specific surface antigen on the tumor cell (5). This method circumvents the signaling pathways that typically occur between the T cell and the antigen presenting tumor cell, rendering them resistant to immunosuppression. Because it requires genetic engineering of the patients own cells and due to potentially dangerous side effects of cytokine-release syndrome that can occur (6), CAR T therapy requires close individual monitoring that would not be necessary with more traditional drug therapies. The ability of CAR T cells to fight solid tumors such as ovarian cancer is still being evaluated.

Another method for fighting cancer that has shown potential is the use of oncolytic viruses (OVs) or viral vectors. These viruses are thought to act by specifically infecting and killing cancer cells. As cancer cells are lysed, dendritic cells are able to pick up released tumor antigens and generate a better anti-tumor immune response. However, the viruses and viral vectors were found to accumulate in the lymph nodes or other organs and at locations other than the intended target tumor. Thus, there remains a need to provide a method for safe and effective cancer treatment and prevention that does not have the danger and drawback as discussed above.

3. SUMMARY

Described herein are fusion proteins comprising one or more tumor associated antigens and one or more modified alpha virus surface glycoproteins. Also described are the multimeric complexes, nucleic acids encoding the modified fusion proteins, amino acid sequences of the fusion proteins, antibodies to the fusion proteins, and uses thereof. In certain embodiments, the alpha virus is Sindbis alpha virus or chikungunya virus. In certain embodiments, the modified alpha virus surface glycoprotein is E1, E2 or 6K. In certain embodiments, the modified alpha virus surface glycoprotein is E1 and E2. In certain embodiments, provided herein are modified alpha virus polyprotein. In certain embodiments, the polyprotein is E3 or capsid protein. Provided herein are fusion proteins comprising one or more modified alpha virus surface glycoproteins and other proteins as disclosed in table 3 of the NCI Pilot Project to Prioritize Cancer Antigens Clin. Cancer Res 2009; 15:5323-5337. Also described herein is a recombinant fusion protein comprising a modified alpha virus surface glycoproteins and one or more genes or gene segments. In certain embodiments, the fusion proteins are encoded by a construct comprising gene or gene segments of the tumor associated antigen that are inserted internally or terminally of gene segments of the alpha virus surface glycoproteins. In certain embodiments, the gene or gene segments are one or more tumor associated antigens. In certain embodiments, the fusion protein is a monomer, complex, conjugate. In certain embodiments, the fusion protein is capable of forming a dimer, trimer or multimer.

Also described herein are fusion proteins comprising one or more viral antigens and one or more modified alpha virus surface glycoproteins.

Also described herein are methods of treatment or prevention of a disease by administration of the fusion protein comprising one or more tumor associated antigen and one or more modified alpha virus surface glycoproteins. In certain embodiment, the method disclosed herein is for the treatment of a subject to activate a suppressed immune system. In certain embodiments, the treatment is for cancer patients. In certain embodiments, the treatment comprises infiltrating and killing tumor cells. In certain embodiments, the treatment comprises killing latent viral infected cells.

In one embodiment, disclosed is a method for treating cancer in a subject, comprising administering to the subject in need thereof, a fusion protein wherein the fusion protein consists essentially of alpha virus surface membrane glycoprotein E1, E2 and at least one linker, wherein the fusion protein stimulates an immune response when administered to the subject.

Described herein is a kit containing the fusion protein for the prevention and treatment of diseases.

The methods disclosed comprises administration of a fusion protein comprising one or more tumor associated antigens and one or more modified alpha virus surface glycoproteins. In certain embodiments, the modified alpha virus surface glycoprotein is a monomer, complex, fusion, conjugate. In certain embodiments, the fusion protein is capable to form a dimer, trimer or multimer. The fusion protein comprising one or more tumor associated antigens and one or more modified alpha virus surface glycoprotein is useful for one or more of the following: (i) excite/activate the human immune system; (ii) stimulate/activate growth of human T cells; (iii) excite/activate human hemopoietic cells, including T cells, NK cells, B cells, dendritic cells, regulatory T cells, macrophages, erythrocytes, etc.; (iv) release T cells from anergy; (v) overcome breakpoint inhibition of T cells; (vi) treat or prevent cancer; and (vii) latent viral infected cells. In certain embodiments, the method comprises administration of the fusion protein comprising a tumor associated antigen and modified alpha virus surface glycoprotein to a subject in need thereof to: (i) excite/ activate the human immune system; (ii) stimulate/activate growth of human T cells; (iii) excite/activate human hemopoietic cells, including T cells, NK cells, B cells, dendritic cells, regulatory T cells, macrophages, erythrocytes, etc.; (iv) release T cells from anergy; (v) overcome breakpoint inhibition of T cells; and (vi) treat or prevent cancer. In certain embodiment, the method disclosed herein is for the treatment of a subject to activate a suppressed immune system in cancer patients to infiltrate and kill tumor cells. In other embodiments, the fusion protein comprising one or more viral antigens and one or more modified alpha virus surface glycoprotein which is useful for killing latent viral infected cells.

4. BRIEF DESCRIPTION OF THE FIGURES

Figure 1B:
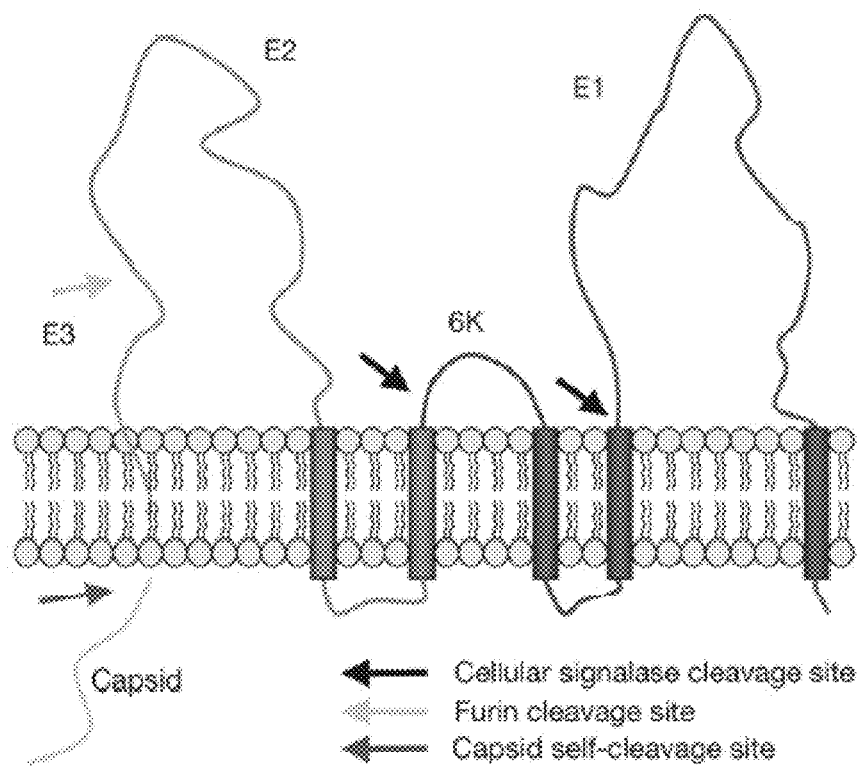

FIGS. 1A-B The Structural Proteins of an Alpha Virus. (A) The cryo-EM density of Sindbis virus showing T=4 symmetry. The four E2 molecules in one asymmetric unit. These give rise to one trimeric spike on each icosahedral three-fold axis and one generally positioned spike. (B) Threading of the Sindbis virus structural polyprotein through an endoplasmic reticulum membrane showing the position of the capsid, E3. E2, 6K and E1 proteins. (Li, L. et al. Structural changes of envelope proteins during alphavirus fusion. *Nature* 468, 705-708 (2010)).

Figures 2A, 2B:
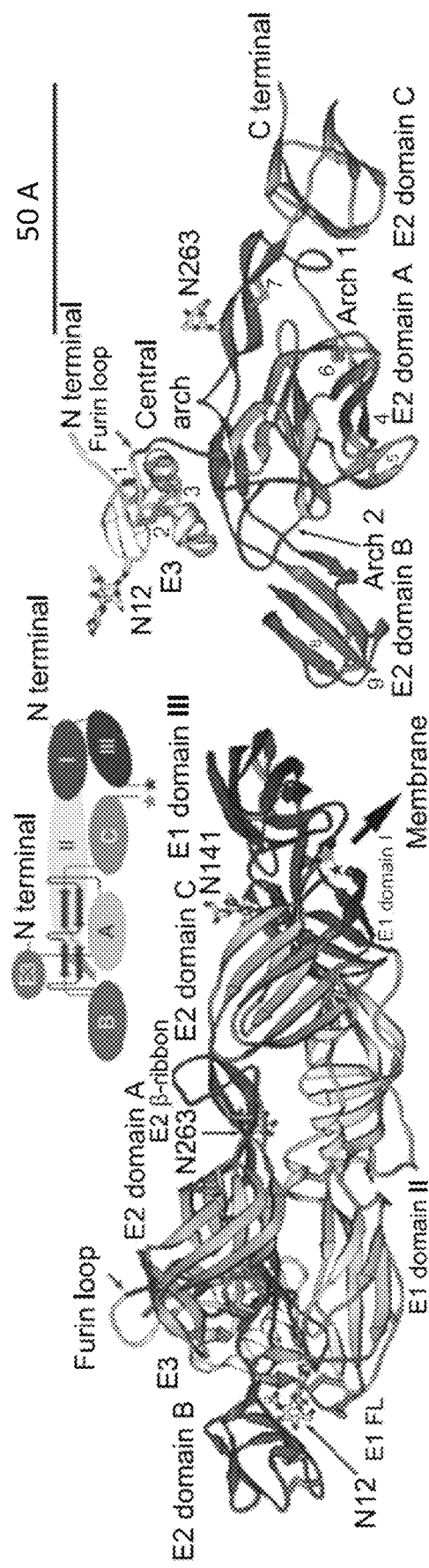

FIGS. 2A-B Domain structure of the glycoprotein spike. (A) Ribbon diagram of the p62-E1 heterodimer. E1 domains I, II and III are shown, as well as the fusion loop (FL). E3 and E2 domain A, B, C and the β-ribbon are also shown. The N-linked glycans are shown in ball and stick, and labeled. The disulphides are depicted as sticks. The arrow (next to the stars indicating the C termini of p62 and E1, respectively) points to the viral membrane. Inset, schematic diagram, with the heterodimer 'plate' drawn 'untwisted', showing how the domains are positioned with respect to one another and their connectivity. (B) p62 organization, oriented roughly at 90 degrees from a to show E3. (Voss J E, et al. Glycoprotein organization of chikungunya virus particles revealed by x-ray crystallography. *Nature* 468, 709-712 (2010)).

Figure 3:
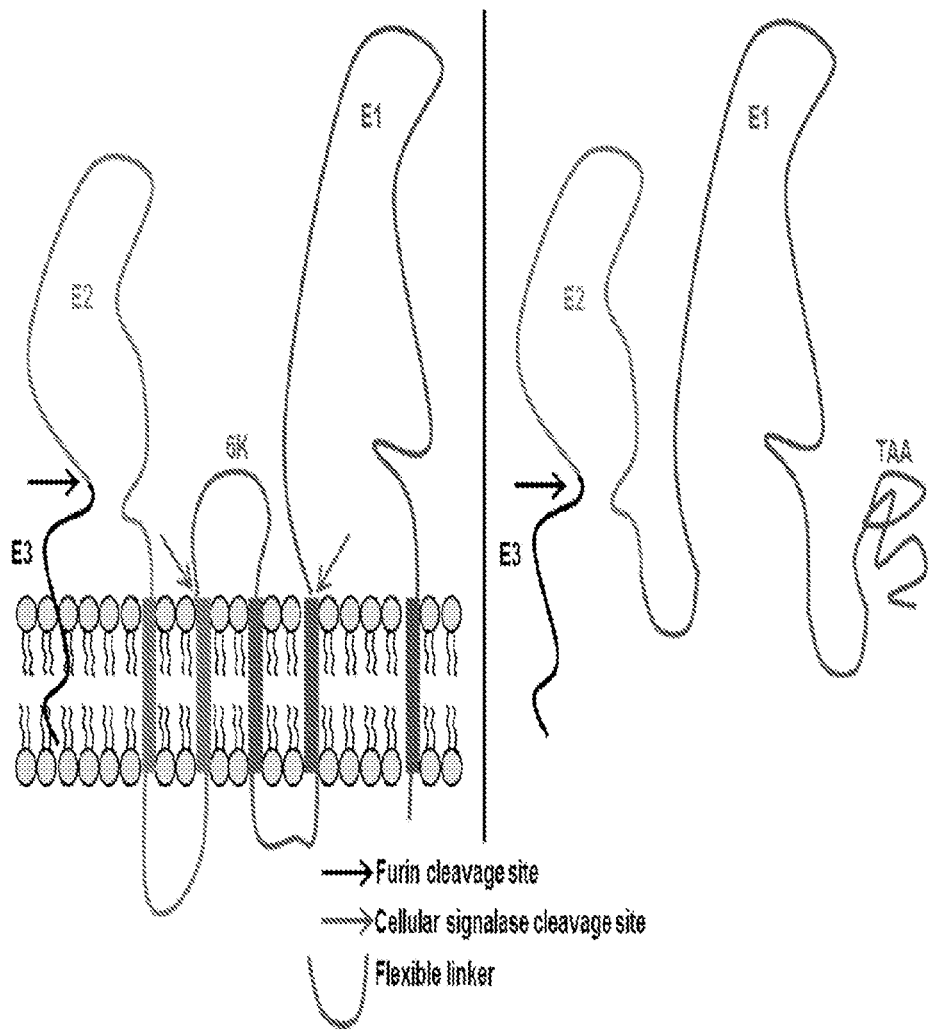

FIG. 3 Structure of engineered recombinant Sindbis VGP. Left, complete structural protein composition encoded by SINV. Right, engineered VGP lacking transmembrane domains and 6K region, linked with a Tumor Associated Antigen (TAA).

Figure 4A:
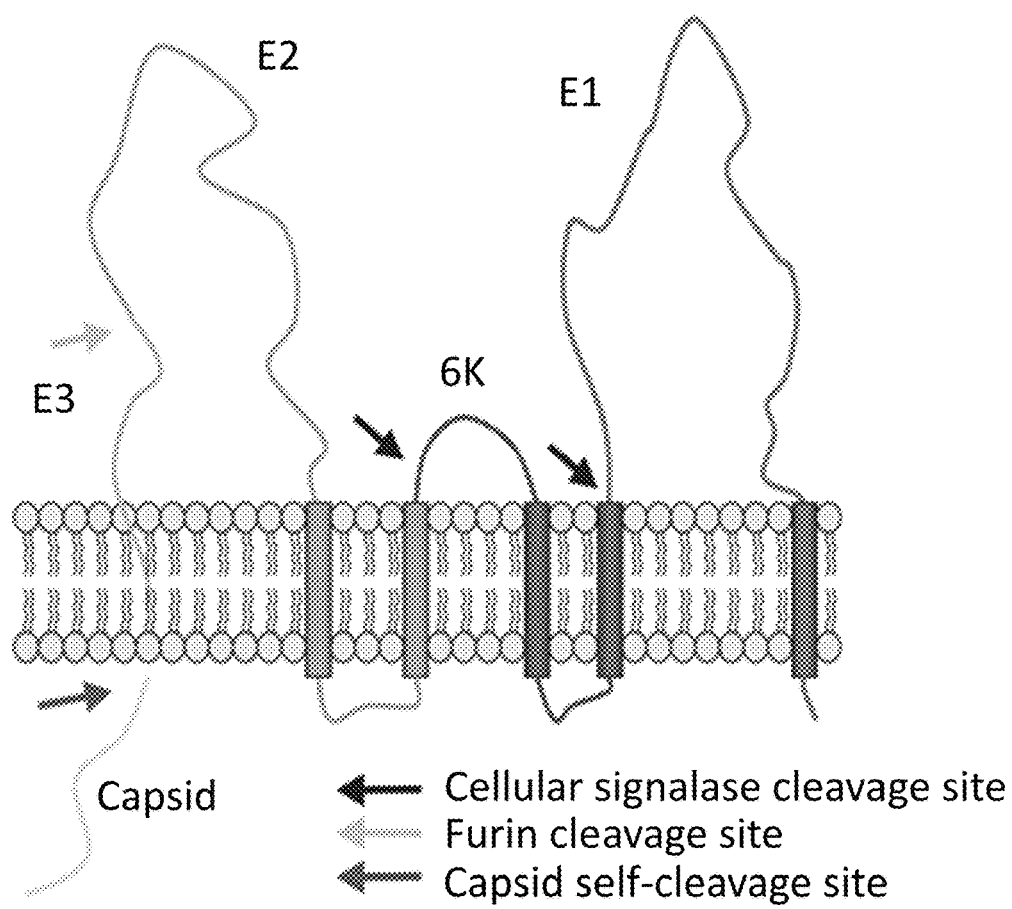
Figure 4B:
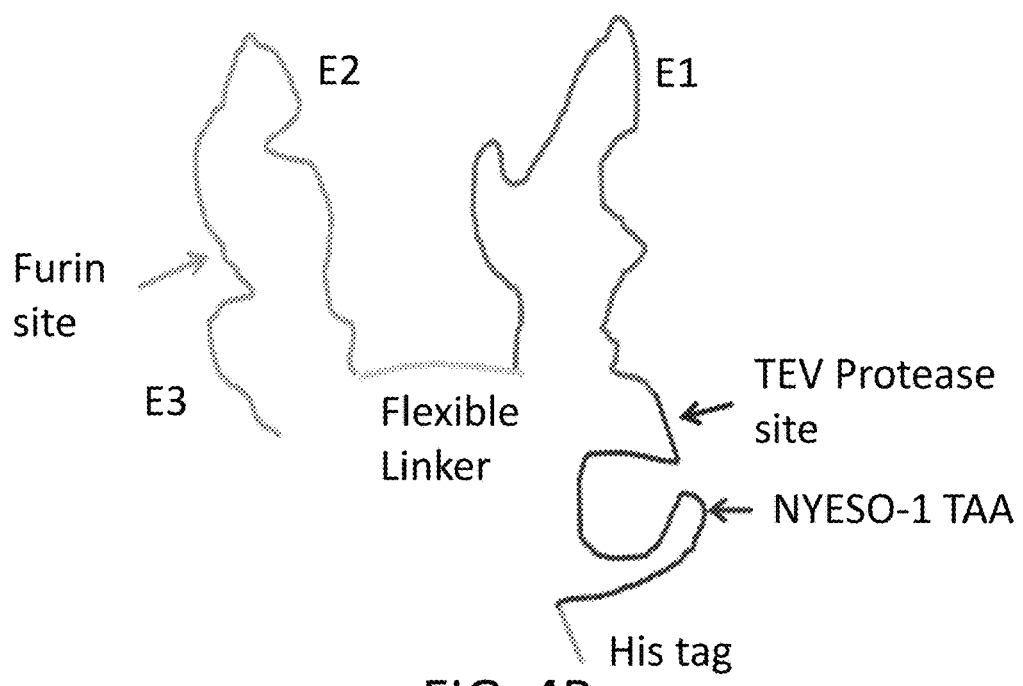
Figure 4C:
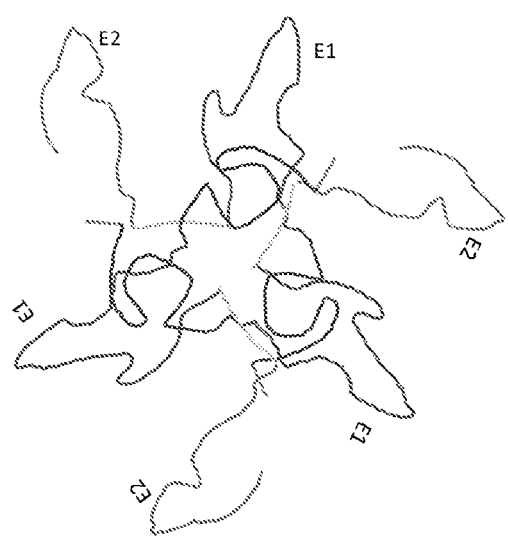

FIGS. 4A-C. Engineered Viral Glycoprotein Construct E2 E1 Dimer and TAA form spike trimer Transmembrane and 6K regions are removed and E2 and E1 are joined by a flexible linker. The E3 sequence acts as an ER targeting sequence and aids in E2/E1 dimerization. TAA is added to C-terminus of E1 with another flexible linker and a protease cleavage site. VGPs trimerized forming soluble spike carrying TAAs upon secretion from golgi.

FIG. 5 Amino acid sequence of an example of fusion protein E3-E2-linker-E1-TEV-linker-NY-ESO-1-6× His. E3-amino acid residues at positions 1-65; E2-amino acid residues at positions 66-429; linker-amino acid residues at positions 430-448; E1-amino acid residues at positions 449-854; TEV-linker-amino acid residues at positions 855-876; and NY-ESO-1 peptide fragment amino acid residues at positions 877-978; 6× His-amino acid residues at positions 979-984. Bolded N is glycosylation sites: amino acid residues at positions 261, 383, 587 and 693.

Figure 7:
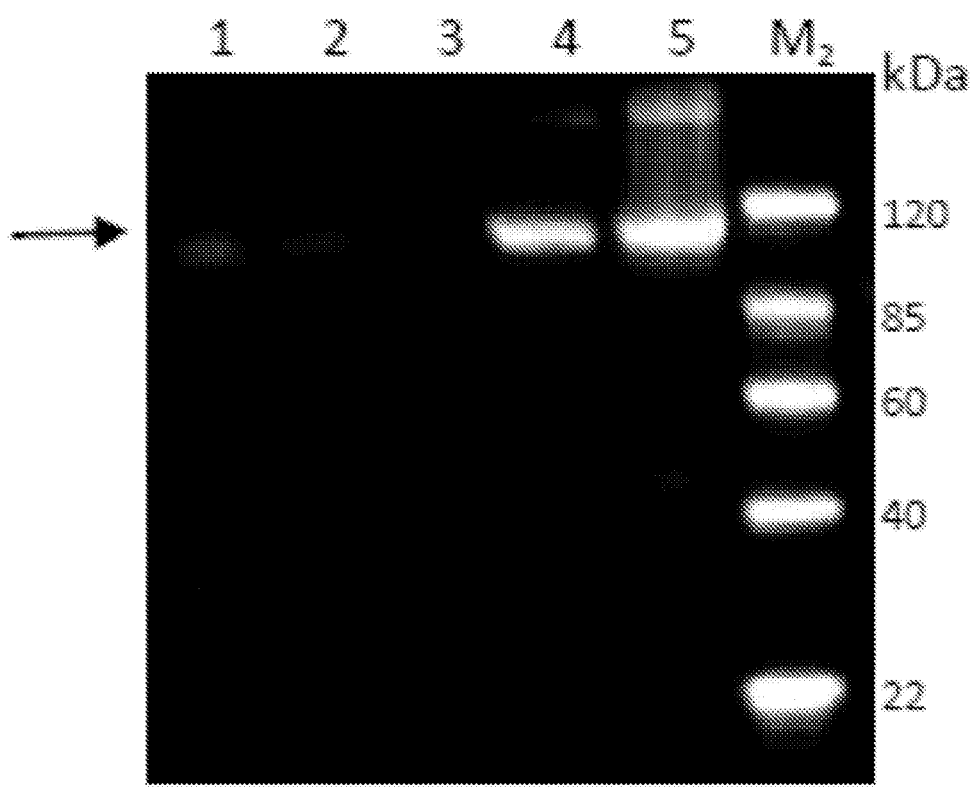

FIG. 6 Nucleic acid sequence of an example of fusion protein E3-E2-linker-E1-TEV-linker-NY-ESO-1-6× His FIG. 7 Western Blot of purified fusion protein Supernatant was harvested from 100 ml culture and protein was purified by Ni affinity chromatography. Predicted molecular weight: 106.8 kDa Lane M2: Easy western marker
Lane 1: Medium of cell lysate
Lane 2: Flow through
Lane 3: Eluted with 20 mM imidazole
Lane 4: Eluted with 500 mM imidazole
Lane 5: Resins after elution
Antibody: anti-His antibody (Genscript, Cat. No. A00186)

FIGS. 8A-F. Amino acid sequences of antigens useful for making the presently disclosed fusion proteins (SEQ ID NOS: 3-11).

FIG. 9. Full Sindbis structural protein sequence (Capsid, E3, E2 Ectodomain, E2 Transmembrane Domain, 6K, E1 Ectodomain, E1 Transmembrane Domain) SEQ ID NO:12.

4.1 DEFINITIONS

As used herein, the term "alphavirus" has its conventional meaning in the art, and includes the various species such as VEE, SFV, Sindbis, Ross River Virus, Western Equine Encephalitis Virus, Eastern Equine Encephalitis Virus, Chikungunya, S.A. AR86, Everglades virus, Mucambo, Barmah Forest Virus, Middelburg Virus, Pixuna Virus, O'nyong-nyong Virus, Getah Virus, Sagiyama Virus, Bebaru Virus, Mayaro Virus, Una Virus, Aura Virus, Whataroa Virus, Banbanki Virus, Kyzylagach Virus, Highlands J Virus. Fort Morgan Virus, Ndumu Virus, and Buggy Creek Virus. In certain embodiments, the alphaviruses used in the constructs and methods of the present disclosure are VEE, S.AAR86, Sindbis (e.g. TR339, see U.S. Pat. No. 6,008,035), and SFV.

The term adjuvant refers to any substance whose admixture with an administered immunogenic determinant/antigen/nucleic acid construct increases or otherwise modifies the immune response to said determinant.

The term amino acid refers to synthetic or naturally occurring amino carboxylic acid, including any amino acid occurring in peptides and polypeptides including proteins and enzymes synthesized in vivo thus including modifications of the amino acids. The term amino acid is herein used synonymously with the term "amino acid residue" which is meant to encompass amino acids as stated which have been reacted with at least one other species, such as 2, for example 3, such as more than 3 other species. The generic term amino acid comprises both natural and non-natural amino acids any of which may be in the "D" or "L" isomeric form.

The term antibody refers to immunoglobulin molecules and active portions of immunoglobulin molecules. Antibodies are for example intact immunoglobulin molecules or fragments thereof retaining the immunologic activity.

The term antigen refers to any substance that can bind to a clonally distributed immune receptor (T-cell or B-cell receptor). Usually a peptide, polypeptide or a multimeric polypeptide. Antigens are preferably capable of eliciting an immune response.

The term boost used herein as to boost by a booster shot or dose is to give an additional dose of an immunizing agent, such as a vaccine, given at a time after the initial dose to sustain the immune response elicited by the previous dose of the same agent.

The term carrier refers to an entity or compound to which antigens are coupled to aid in the induction of an immune response.

The term fusion protein refers to a genetically engineered protein that is encoded by a nucleotide sequence made by a joining together two or more complete or partial genes or a series of nucleic acids. Alternatively, a fusion protein may be made by joining together two or more of heterologous peptides.

The term cytokine refers to growth or differentiation modulator, used non-determinative herein. In addition to the cytokines, adhesion or accessory molecules, or any combination thereof, may be employed alone or in combination with the cytokines.

The term Cytotoxic T lymphocytes refers to a sub group of T-cells expressing CD8 along with the T-cell receptor and therefore able to respond to antigens presented by class 1 molecules.

The term delivery vehicle refers to an entity whereby a nucleotide sequence or polypeptide or both can be transported from at least one media to another.

The term fragment refers to a non-full length part of a nucleic acid or polypeptide.

The term subject refers to any species or subspecies of bird, mammal, human, non-human, fish, amphibian, or reptile.

The term isolated used in connection with nucleic acids, polypeptides, and antibodies refers to these having been identified and separated and/or recovered from a component of their natural, typically cellular, environment.

The term nucleic acids, polypeptides, and antibodies are preferably isolated, and vaccines and other compositions of the invention preferably comprise isolated nucleic acids, polypeptides or isolated antibodies.

The term MHC or Major histocompatibility complex refers to two main subclasses of MHC, Class I and Class II.

The term nucleic acid refers to a chain or sequence of nucleotides that convey genetic information. Nucleic acid construct refers to a genetically engineered nucleic acid. Typically comprising several elements such as genes or fragments of same, promoters, enhancers, terminators, polyA tails, linkers, polylinkers, operative linkers, multiple cloning sites (MCS), markers, STOP codons, other regulatory elements, internal ribosomal entry sites (IRES) or others.

The term operative linker refers to a sequence of nucleotides or amino acid residues that bind together two parts of a nucleic acid construct or fusion polypeptide in a manner securing the biological processing of the nucleic acid or polypeptide.

The term pathogen refers to a specific causative agent of disease, especially a biological agent such as a virus, bacteria, prion or parasite that can cause disease to its host, also referred to as an infective agent.

The term "cancer" or "tumor" refers to a neoplasm or tumor resulting from abnormal uncontrolled growth of cells. The term "cancer" encompasses a disease involving both pre-malignant and malignant cancer cells. In some embodiments, cancer refers to a localized overgrowth of cells that has not spread to other parts of a subject, i.e., a benign tumor. In other embodiments, cancer refers to a malignant tumor, which has invaded and destroyed neighboring body structures and spread to distant sites. In yet other embodiments, the cancer is associated with a specific cancer antigen.

As used herein, the term "effective amount" refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In one embodiment, the amount of a therapy is effective to achieve one, two, three or more of the following results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer;

(15) an increase in the time to recurrence of cancer; and (16) an amelioration of cancer-related symptoms and/or quality of life.

The term peptide refers to plurality of covalently linked amino acid residues defining a sequence and linked by amide bonds. The term is used analogously with oligopeptide and polypeptide. The natural and/or non-natural amino acids may be linked by peptide bonds or by non-peptide bonds. The term peptide also embraces post-translational modifications introduced by chemical or enzyme-catalyzed reactions, as are known in the art. The term can refer to a variant or fragment of a polypeptide.

The term pharmaceutical carriers, excipients, or stabilizers are non-toxic to the cell or individual being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLIURONICS™.

The term promoter refers to a binding site in a DNA chain at which RNA polymerase binds to initiate transcription of messenger RNA by one or more nearby structural genes.

The term signal peptide refers to a short sequence of amino acids that determine the eventual location of a protein in the cell, also referred to as sorting peptide.

The term surfactant refers to a surface active agent capable of reducing the surface tension of a liquid in which it is dissolved. A surfactant is a compound containing a polar group which is hydrophilic and a non-polar group which is hydrophobic and often composed of a fatty chain.

The term vaccine refers to a substance or composition capable of inducing an immune response in an animal. Also referred to as an immunogenic composition. An immune response being an immune response (humoral/antibody and/or cellular) inducing memory in an organism, resulting in the infectious agent, being met by a secondary rather than a primary response, thus reducing its impact on the host organism. A vaccine may be given as or prophylactic and/or therapeutic medicament. The composition may comprise one or more of the following: VGP conjugated to one or more tumor associated antigen(s), nucleic acid constructs comprising VGP operatively linked to one or more antigens, carriers, adjuvants and pharmaceutical carriers.

The term variant refers to a nucleic acid or polypeptide that displays a certain degree of sequence homology/identity to a given reference nucleic acid or polypeptide but is not identical to said reference nucleic acid or polypeptide.

5. DETAILED DESCRIPTION

5.1 Fusion Protein Comprising Modified Alphavirus Glycoproteins and Antigens Like all alphaviruses, the Sindbis genome encodes for 4 nonstructural proteins (nsP1-4) responsible for RNA replication, and 5 structural proteins (capsid, E3, E2, 6K, and E1). The structural proteins are expressed as a single polyprotein that is cleaved by cellular proteases to generate the mature proteins (see FIG. 1). The capsid protein forms an internal core surrounding the viral genome and interacts with the cytoplasmic tail of the E2 envelope glycoprotein (7). The E3 protein acts a signal sequence for pE2, the precursor protein composed of E3 and E2, mediates proper E2 folding, and is necessary for the heterodimerization of E2 with E1 (7). During protein processing in the golgi, E3 is cleaved by furin and shed upon virus budding from the cell (7). Sindbis Virus ("SINV") E2 is a transmembrane glycoprotein with 2 N-linked glycosylation sites at 196 and 318 (8). The 6K protein acts as a signal sequence for E1, is cleaved from E1 and E2 by signal peptidase, and is minimally present in the mature virion. SINV E1 is a transmembrane glycoprotein with 2 N-linked glycosylation sites at 139 and 245 (8). As the virus buds from the cell, the capsid is contained within the viral envelope derived from the host cell plasma membrane. The E2/E1 heterodimer exists as a trimeric spike on the surface of the viral envelope. The E2 region is responsible for interacting with receptors on target cells, while E1 triggers membrane fusion under the low pH conditions of late endosomes and lysosomes (8).

Described herein is a fusion protein comprising modified viral glycoproteins (VGPs), the E1 and E2 proteins expressed together as a single recombinant protein (see FIG. 3) that are conjugated to tumor specific antigens forming a fusion protein VGP-TAA for therapy. In specific embodiments, the fusion protein does not contain transmembrane protein, 6K regions and non-structural proteins. In specific embodiments, the expression vector that expresses the fusion protein is not a viral vector. In one embodiment, the fusion protein has the amino acid sequence of SEQ ID NO: 1. In certain embodiments, the fusion protein has the amino acid sequence of SEQ ID NO:1 with the following modifications: (1) deletion of the following amino acid residues: 1-65, 979-978. The fusion protein is a recombinant protein that is encoded by a nucleotide having a nucleotide sequence of the viral surface membrane glycoprotein that is operatively linked to one or more tumor associated antigen. In certain embodiments, the one or more tumor associated antigens are disclosed in table 3 of the NCI Pilot Project to Prioritize Cancer Antigens Clin. Cancer Res 2009; 15:5323-5337.

In certain embodiments, the tumor associated antigen portion of the fusion protein may have an amino acid sequence having at least a % identity to SEQ ID NOs: 3-11. In certain embodiments, the tumor associated antigen portion of the fusion protein may have an amino acid sequence having at least a % identity to SEQ ID NOs: 1 at amino acid positions 877-978.

In certain embodiments, the tumor associated antigen includes at least 7, 8, 9, 10, 12, 14, 16, 18, 20, 25, 30, 35, 40, 50, 60, 70, 80, 90, 100, 150, 200, 250 or more consecutive amino acids of any of SEQ ID NOs: 3-11, wherein the consecutive amino acids is immunogenic.

In certain embodiments, the tumor associated antigen comprises 10-20, 20-30, 30-50, 50-150, 150-200, 200-400, 400-500 amino acids from SEQ ID NOs: 3-11. In certain embodiments, the tumor associated antigen does not comprise a full length protein from SEQ ID Nos: 3-11.

In certain embodiments, the tumor associated antigen has less than 1200 amino acids, less than 1100 amino acids, less than 1000 amino acids, less than 950 amino acids, less than 900 amino acids, less than 850 amino acids, less than 800 amino acids, less than 750 amino acids, less than 700 amino acids, less than 650 amino acids, less than 600 amino acids, less than 590 amino acids, or less than 580 amino acids of the protein from SEQ ID Nos: 3-11.

Tumor associated antigen fragments from SEQ ID NOs 3-11 discussed above include, without limitation, are immunogenic fragments that, when administered to a subject in a suitable composition which can include an adjuvant (including without limitation any of the adjuvants listed or discussed in the section "Immunogenic compositions and medicaments" below), or a suitable carrier coupled to the polypeptide, induces an antibody or T-cell mediated immune response that recognizes the isolated full length polypeptide SEQ ID Nos 3-11, respectively, from which the immunogenic fragment is derived.

Tumor associated antigen may, compared to any one of SEQ ID Nos 3-11, include one or more (e.g. 1, 2, 3, 4, 5, 6, 7, 8, 9, etc.) amino acid substitutions, such as conservative substitutions (i.e. substitutions of one amino acid with another which has a related side chain). Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity.

A polypeptide may include one or more (e.g. 1, 2, 3, 4, 5, 6, 7, 8, 9, etc.) single amino acid deletions relative to any one of SEQ ID Nos 3-11. Similarly, a polypeptides may include one or more (e.g. 1, 2, 3, 4, 5, 6, 7, 8, 9, etc.) insertions (e.g. each of 1, 2, 3, 4 or 5 amino acids) relative to any one of SEQ ID Nos 3-11.

Deletions or substitutions may be at the N-terminus and/or C-terminus, or may be between the two termini. Thus a truncation is an example of a deletion. Truncations may involve deletion of up to 40 (or more) amino acids at the N-terminus and/or C-terminus.

In general, when a polypeptide of the invention comprises a sequence that is not identical to a complete sequence of SEQ ID NOs 3-11 (e.g. when it comprises a sequence listing with <100% sequence identity thereto, or when it comprises a fragment thereof) it is preferred that the polypeptide can elicit an antibody that recognises a polypeptide consisting of the complete SEQ ID sequence i.e. the antibody binds to one or more of said SEQ ID Nos 3-11. Such antibody may bind specifically to SEQ ID Nos 3-11, respectively while not binding to other proteins that are not homologs with affinity significantly higher than the antibody's non-specific affinity to human serum albumin as a non-specific binding reference standard.

A polypeptide of the invention may include a metal ion e.g. a metal ion that is coordinated by one or more amino acids in the polypeptide chain. For instance, the polypeptide may include a monovalent, divalent or trivalent metal cation. Divalent cations are typical, such as Mn2+, Fe2+, Co2+, Ni2+, Cu2+, etc. The divalent cation is preferably Zn2+.

Polypeptides disclosed herein can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). For instance, a polypeptide of the invention may have a lipidated N-terminal cysteine.

Polypeptides disclosed herein can be prepared by various means (e.g. recombinant expression, purification from cell culture, chemical synthesis, etc.). Recombinantly-expressed proteins are preferred.

Polypeptides disclosed herein are preferably provided in purified or substantially purified form i.e. substantially free from other polypeptides (e.g. free from naturally-occurring polypeptides), particularly from other E. coli or host cell polypeptides, and are generally at least about 50% pure (by weight), and usually at least about 90% pure i.e. less than about 50%, and more preferably less than about 10% (e.g. 5%) of a composition is made up of other expressed polypeptides. Thus the antigens in the compositions are separated from the whole organism with which the molecule is expressed.

An epitope within a tumor associated antigen from a peptide fragment may be a B-cell epitope and/or a T-cell epitope. Such epitopes can be identified empirically (e.g. using PEPSCAN or similar methods), or they can be predicted (e.g. using the Jameson-Wolf antigenic index, matrix-based approaches, MAPITOPE, TEPITOPE, neural networks, OptiMer & EpiMer, ADEPT, Tsites, hydrophilicity, antigenic index, etc.). Epitopes are the parts of an antigen that are recognised by and bind to the antigen binding sites of antibodies or T-cell receptors, and they may also be referred to as "antigenic determinants".

Any of the polypeptides disclosed herein have utility as components of vaccines. Thus in another embodiment, the isolated or recombinant polypeptide will be with an adjuvant.

In one embodiment, the fusion protein comprises one or more antigenic proteins or peptide or fragment of an antigenic protein, which protein is a tumor associated antigen. Many proteins have been identified and linked to certain types of cancer; these are referred to as tumor associated antigens. In general, any antigen that is found to be associated with cancer tumors may be used. In certain embodiments, the tumor associated antigen is WT1 (UniProt Knowledgebase, MUC1 (P15941), LMP2 (P13285), HPV16 E6(P03126) and E7(P03129), HPV18 (E6-P06463) and E7(P06788), RGL4 (Q8IZJ4), EGFRvIII (P0533), HER-2/neu (P04626), MAGE A3 (Q53EX0), PSMA (Q04609), CEA (P06731), MelanA/MART (Q16655), gp100 (P40967), Proteinase3 (PRI) (P24158), bcr-abl fusion, bcr (P11274), abl (P00519), Tyrosinase (P14679), Survivin (015392), PSA (P07288), hTERT (014746), EphA2 (P29317), PAP (P15309), ML-IAP (Q96CA5), AFP (P02771), EpCAM (P16422), TMPRSS2/ERG fusion, TMPRSS2 (015393), ERG (P11308), PAX3 (P23760), ALK (Q9UM73), Androgen receptor (P10275), Cyclin B1 (P14635), MYCN (P04198), RhoC (P08134), TRP-2 (P40126), Mesothelin (Q13421), PSCA (043653), MAGE A1 (P43355), CYPIB1 (Q16678), PLACl (Q9HBJO), BORIS (Q8NI51), NY-BR-1 (Q9BXX3), RGS5 (015539), SART3 (Q15020), Carbonic anhydrase IX (Q16790), PAX5 (Q02548), OY-TES1 (Q8NEB7), Sperm protein 17 (Q15506), LCK (P06239), HMWMAA (Q6UVK1), AKAP-4 (Q5JQC9), SSX2 (Q16385), XAGE 1 (Q9HD64), Legumain (Q99538), Tie 2 (Q02763), VEGFR2 (P35968), PDGFR-0 (P09619), and Fos-related antigen 1 (P15407).

In certain embodiments, one or more of the alpha virus surface membrane glycoproteins is operatively linked to one or more tumor associated antigen. In one embodiment, the tumor specific antigen is the primary antigenic region of the cancer-testis antigen NY-ESO-1. In certain embodiments, the tumor specific antigen includes the list of target human TAAs for cancer immunotherapy (9). In a specific embodiment, the SINV VGP recombinant protein is conjugated to the primary antigenic region of the NY-ESO-1 protein to form a fusion protein.

In certain embodiments, additional N-linked glycosylation sites may be engineered into the viral glycoprotein. N-linked glycans are attached to an asparagine side chain that is present as a part of Asparagine-X-Serine/Threonine sequence, where X is any amino acid except proline.

The disclosure also relates to a nucleic acid construct encoding a fusion protein comprising one or more tumor associated antigen and one or more alpha virus surface membrane glycoprotein having the amino acid sequence identified in SEQ ID NO: 1 or a fragment thereof. In certain embodiments, the fragment has 40-80, 80-150, 150-200, 200-300, 300-400, 400-500, 500-600, 600-700, 700-800, 800-850, 850-900 amino acid residues. In certain embodiments, the fragment is at least 85%, 90%, 95%, 99% identical to SEQ ID NO: 2. In certain embodiments, the tumor associated antigens are full length proteins. In certain embodiments, the tumor associated antigens are fragments of a full length protein. In certain embodiments, the fragment has 5-10, 10-20, 20-30, 30-40, 40-80, 80-150, 150-200, 200-300, 300-400, 400-500, 500-600 amino acid residues. In certain embodiments, the fragment is at least 85%, 90%, 95%, 99% identical to wild type tumor associated antigen. The identity/homology between amino acid sequences may be calculated using well known scoring matrices such as any one of BLOSUM 30, BLOSUM 40, BLOSUM 45, BLOSUM 50. BLOSUM 55, BLOSUM 60, BLOSUM 62, BLOSUM 65, BLOSUM 70, BLOSUM 75, BLOSUM 80. BLOSUM 85, and BLOSUM 90.

In certain embodiments, the tumor associated antigen is a polypeptide fragment that is at least 10 consecutive amino acids of any of SEQ ID NOS: 3-11, wherein the polypeptide fragment comprises at least 10 consecutive amino acids is immunogenic and the immunogenic polypeptide fragment comprises less than 1100 amino acids of the polypeptide of SEQ ID Nos: 3-11.

In one embodiment, disclosed is an isolated or recombinant fusion protein consisting essentially of alpha virus surface membrane glycoproteins E1, E2 and optionally E3, a linker and at least one tumor associated antigen, wherein the fusion protein stimulates an immune response when administered to a subject. In one embodiment, the fusion protein of comprises an amino acid sequence having at least 98% identity to SEQ ID NO: 1. In one embodiment, the fusion protein comprises at least amino acid residues at positions 66-978 of SEQ ID NO:1. In one embodiment, the fusion protein is encoded by a nucleic acid molecule having at least 95% identity to SEQ ID NO: 2. In one embodiment, the fusion protein further comprising a deletion of amino acid residues at (i) positions 1-65; (ii) positions 979-984; or (iii) positions 1-65 and 979-984, of SEQ ID NO:1. In one embodiment, the E2 comprises an amino acid sequence that is at least 300 amino acid in length and has at least 95% sequence identity to SEQ ID NO:1 at positions 66-429. In one embodiment, the E1 comprises an amino acid sequence that is at least 300 amino acid in length and has at least 95% sequence identity to SEQ ID NO:1 at positions 449-854. In one embodiment, the tumor associated antigen is a polypeptide fragment that is at least 10 consecutive amino acids of any of SEQ ID NOS: 3-11, wherein the polypeptide fragment comprises at least 10 consecutive amino acids is immunogenic and the immunogenic polypeptide fragment comprises less than 1100 amino acids of the polypeptide of SEQ ID Nos: 3-11.

One skilled in the art would also know that the above can be applied to viral antigens. Thus, in certain embodiments, the tumor associated antigens are replaced by viral antigens. In certain embodiments, the fusion protein comprises one or more viral antigens and one or more alpha virus surface membrane glycoproteins. In certain embodiments, the viral antigen is HSV-1 glycoprotein B (P06437), glycoprotein E (P04488), HIV gag-pol (P04585), chickenpox (Varicella zoster) glycoprotein B (Q4JR05) or glycoprotein E (Q9J3M8).

5.2 Method of Making Vgp-Taa

Provided herein is a process for producing a fusion protein, comprising the step of culturing a host cell transformed with nucleic acid encoding the fusion protein under conditions which induce polypeptide expression. The polypeptide may then be purified e.g. from culture supernatants.

The invention provides a process for producing a polypeptide of the invention, comprising the step of synthesizing at least part of the polypeptide by chemical means.

Any and all of the foregoing proteins, polypeptides, hybrid polypeptides, epitopes and immunogenic fragments may be in any one of a number of forms including, without limitation, recombinant, isolated or substantially purified (from materials co-existing with such proteins, polypeptides, hybrid polypeptides, epitopes and immunogenic fragments in their natural state).

In one aspect, the fusion protein as disclosed herein is encoded by a nucleic acid construct comprising one or more viral surface membrane glycoproteins operatively linked to one or more tumor associated antigen. The fusion protein is a recombinant protein that is encoded by a nucleotide having a nucleotide sequence of the viral surface membrane glycoprotein that is operatively linked to one or more tumor associated antigen. In one embodiment, the nucleic acid construct is an expression vector. In one embodiment, the expression vector is non-viral, viral or a plasmid. In certain embodiments, the expression vector comprises genes or fragment of genes, promoters, enhancers, termination signals, poly-A tails, linkers, polylinkers, operative linkers, multiple cloning sites, markers, STOP codons, internal ribosomal entry sites, host homologous sequences for integration or other defined elements. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989).

In some embodiments, nucleic acid of the invention hybridizes to a target under low stringency conditions; in other embodiments it hybridizes under intermediate stringency conditions; in preferred embodiments, it hybridizes under high stringency conditions. An exemplary set of low stringency hybridization conditions is 50° C. and 10×SSC. An exemplary set of intermediate stringency hybridization conditions is 55° C. and 1×SSC. An exemplary set of high stringency hybridization conditions is 680° C. and 0.1×SSC.

The invention includes nucleic acid comprising sequences complementary to these sequences (e.g. for antisense or probing, or for use as primers).

Nucleic acids of the invention can be used in hybridization reactions (e.g. Northern or Southern blots, or in nucleic acid microarrays or 'gene chips') and amplification reactions (e.g. PCR, SDA, SSSR, LCR, TMA, NASBA, etc.) and other nucleic acid techniques.

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably provided in purified or substantially purified form i.e. substantially free from other nucleic acids (e.g. free from naturally-occurring nucleic acids), particularly from host cell nucleic acids, generally being at least about 50% pure (by weight), and usually at least about 90% pure.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acid of the invention may be attached to a solid support (e.g. a bead, plate, filter, film, slide, microarray support, resin, etc.). Nucleic acid of the invention may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids, as mentioned above. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T).

Nucleic acids of the invention can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesized in part or in whole using chemical means.

The invention provides vectors comprising nucleotide sequences of the invention (e.g. cloning or expression vectors) and host cells transformed with such vectors.

Nucleic acid amplification according to the invention may be quantitative and/or real-time.

For certain embodiments of the invention, nucleic acids are preferably at least 7 nucleotides in length (e.g. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 100, 110, 120, 130, 140, 150, 160, 170, 180, 190, 200, 225, 250, 275, 300 nucleotides or longer).

For certain embodiments of the invention, nucleic acids are preferably at most 500 nucleotides in length (e.g. 450, 400, 350, 300, 250, 200, 150, 140, 130, 120, 110, 100, 90, 80, 75, 70, 65, 60, 55, 50, 45, 40, 39, 38, 37, 36, 35, 34, 33, 32, 31, 30, 29, 28, 27, 26, 25, 24, 23, 22, 21, 20, 19, 18, 17, 16, 15 nucleotides or shorter).

Primers and probes of the invention, and other nucleic acids used for hybridization, are preferably between 10 and 30 nucleotides in length (e.g. 10, 11, 12, 13, 14, 15, 16, 17, 18, 19, 20, 21, 22, 23, 24, 25, 26, 27, 28, 29, or 30 nucleotides).

In certain embodiments, the disclosed nucleic acid construct that encodes the fusion protein comprises one or more alpha virus surface membrane glycoprotein conjugated to one or more tumor associated antigen through an operative linker. In one embodiment, the linker is a direct link. In one embodiment, the linker is a spacer region. By the term operative linker is understood a sequence of nucleotides or amino acid residues that bind together two parts of a nucleic acid construct or fusion protein in a manner securing the biological processing of the nucleic acid or the protein. If the operative linker is a direct link, the two nucleic acids each encoding either an open reading frame or a fragment of an open reading frame are placed immediately adjacent to each other and thereby also in frame. If the operative linker is mediated by a spacer region, a series of nucleotides are inserted between the nucleotides encoding the one or more alpha virus surface membrane glycoprotein and the one or more tumor associated antigen. In certain embodiments, the operative linker comprises at least one polylinker or multiple cloning site (MCS).

Examples of nucleic acid constructs are provided in FIG. 6, as well as in the sequences identified as SEQ ID NO:2. The partial vector sequences of SEQ ID NO: 1 were generated by subcloning various elements as described in the above. These partial sequences are all inserted into pUC57, then transferred to the pFastBac1. See GenBank accession number AY598466.

In one embodiment, the transmembrane and 6K regions are removed and E2 and E1 are joined by a flexible linker. The E3 sequence acts as an ER targeting sequence and aids in E2/E1 dimerization. TAA is added to C-terminus of E1 with another flexible linker and a protease cleavage site. VGPs trimerize forming soluble spike carrying TAAs upon secretion from golgi. In one embodiment, the protein is made in insect cells by baculovirus expression system.

In one embodiment, engineered recombinant alphavirus glycoproteins (VGPs) are produced using the baculovirus expression system and have comparable targeting specificity to the native virus.

In certain embodiments, proper glycosylation is maintained in the fusion protein which does not elicit an undesirable immune response.

In certain embodiments, the fusion protein is soluble. In certain embodiments, the fusion protein is insoluble.

In certain embodiments, the method disclosed herein is a direct killing of tumor cells. In certain embodiments, the method disclosed herein is an induction of apoptosis which occurs at viral entry and does not require viral replication. In certain embodiments, the glycoproteins on the fusion protein induce apoptosis. In certain embodiments, release of other tumor associated antigens effectuate tumor killing. In certain embodiments, presentation of viral proteins on tumor cell surface induce cytotoxic T cell and/or NK responses.

In certain embodiments, the recombinant expression vector is delivered via certain delivery vehicles. The delivery vehicles may be RNA or DNA based vehicles, lipid based vehicles, cell based vehicles, biodegradable polymer microspheres, liposomes, colloidal gold particles or lipopolysaccharides. Naked DNA may also be delivered by mechanical or electrical techniques such as ballistic transfer using particle bombardment equipment such as a gene gun.

In one embodiment, VGP-TAA fusion protein is generated by recombinant expression vector. In one embodiment, the Sindbis fusion glycoprotein is generated by baculovirus expression in Sf9 insect cells. The baculovirus system is a versatile and powerful eukaryotic vector system using insect cells for recombinant protein expression (10), offering numerous advantages over other expression vector systems. Since baculoviruses can only infect specific invertebrate species, they are nonpathogenic to mammals. Unlike bacterial protein expression, proteins expressed in the baculovirus system are processed, folded, and modified similarly to those produced in a mammalian expression system. Additionally, baculovirus-expressed proteins are easily scaled up to produce large quantities of recombinant protein. Insect cell lines are available that grow well in suspension cultures, allowing the production of recombinant proteins in large-scale bioreactors. Use of the baculovirus system provides another distinct advantage specific for our protein. While both insect and mammalian cells are both capable of making N-linked glycosylations, the specific glycosylation pathway is different. N-glycans produced in insect cells can have either a high-mannose or paucimannosidic structure, both of which have terminal mannose residues (11). N-glycans produced in mammalian cells can have either a high-mannose structure or a complex structure terminating in galactose and sialic acid (11). The gene encoding the VGP is produced through gene synthesis and codon-optimized for insect cell expression. The recombinant fusion protein composed of the ectodomains of the pE2 and E1 Sindbis glycoproteins connected by a flexible linker and linked to a TAA by a second linker (see FIG. 3). In one embodiment, the TAA is NY-ESO-1. In other embodiment, other TAA is inserted to the coding sequence. In certain embodiments, a construct is generated with two or more TAAs in tandem, which could result in a more potent immune response.

In certain embodiments, any type of immune response e.g. T cell mediated and antibody mediated responses can be initiated with epitopes of antigens having various strengths to elicit an immune response. In certain embodiments, the fusion protein successfully elicit an immune response against tumor associated antigen that are known to be too weak using conventional immunization methods. In certain embodiments, the fusion protein as disclosed herein successfully elicit immune response that are 5-10 folds, 10-20 folds, 20-30 folds, 30-50 folds, 50-100 folds, 100-500 folds, 500-1,000 folds greater than conventional immunization methods. Saroja, Laskshmi, and Bhaskaran. Int J Pharm Investig. 2011.

In certain embodiment, 2, 3, 4, 5, 6, 7, 8, 9, 10, 11, 12, 20, 30, 40, 50 or more TAA are conjugated to the VGP. The E3 component of pE2 acts as a signal peptide for secretion of the protein, assists in the binding of E1 and E2, and is cleaved from the mature protein by furin (7). The mature secreted protein forms a trimer of the heterodimeric complex of E2 and E1, mimicking the trimeric glycoprotein spike observed on the SINV envelope. The second flexible linker allows proper folding of NY-ESO-1 without interfering with the multimerization of E2/E1. In certain embodiment, the TAA contains amino acid residues 1-180 of NY-ESO-1. In other embodiment, the TAA contains amino acid residues 81-180 of NY-ESO-1. In certain embodiment, a His-tag is added to the C-terminus of the protein for purification purposes. The fusion protein is analyzed to determine its multimeric structure by non-denaturing gel and size-exclusion chromatography. The fusion protein is analyzed by ELISA and western blot assays specific. The fusion protein has several antigenic targets (NY-ESO-1, His-tag, and SINV E1 and E2) that could be detected with commercial antibodies. In certain embodiment, the TAA is RGL4. In certain embodiment, the TAA is E6 protein of the human papiloma virus. In certain embodiment, the TAA is E7 protein of the human papiloma virus.

Also disclosed is a cell comprising the nucleic acid construct which encode the fusion protein. Such a recombinant cell can be used as a tool for in vitro research, as a delivery vehicle for the nucleic acid construct or as part of a gene therapy regimen.

Also disclosed is an antibody or binding fragments that immunospecifically bind the fusion protein disclosed herein. In certain embodiments, the antibody is immunoglobulin molecules and active fragments thereof that immunospecifically binds the antigen. The antibodies and binding fragments may be used for immunization of a subject. The antibodies and binding fragments may be used in an assay for detecting the antigen.

5.3 Immunogenic Compositions and Medicaments

Polypeptides of the invention are useful as active ingredients (immunogens) in immunogenic compositions, and such compositions may be useful as vaccines. Vaccines according to the invention may either be prophylactic (i.e. to prevent infection) or therapeutic (i.e. to treat infection), but will typically be prophylactic.

Immunogenic compositions will be pharmaceutically acceptable. They will usually include components in addition to the antigens e.g. they typically include one or more pharmaceutical carrier(s), excipient(s) and/or adjuvant(s). Also disclosed is a vaccine comprising a nucleic acid sequence encoding a fusion protein comprising one or more alpha virus surface membrane glycoprotein operatively linked to one or more tumor associated antigen. The vaccine may thus comprise a nucleic acid construct or comprises a fusion protein as defined above. The vaccine may furthermore be used as a medicament.

The vaccine composition can be formulated according to known methods such as by the admixture of one or more pharmaceutically acceptable carriers, also known as excipients or stabilizers with the active agent. These excipients may be acceptable for administration to a subject, preferably to vertebrates and more preferably to humans as they are non-toxic to the cell or individual being exposed thereto at the dosages and concentrations employed. In certain embodiments, an acceptable carrier is an aqueous pH buffered solution. Examples of such excipients, carriers and formulation may be found e.g. in Remington's Pharmaceutical Sciences (Maack Publishing Co, Easton, Pa.). Examples of physiologically acceptable carriers include but are not limited to: buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

To formulate a pharmaceutically acceptable composition suitable for effective administration, such compositions will contain an effective amount of the nucleic acid construct, the nucleic acid construct comprised within a delivery vehicle or the fusion protein as described herein. A carrier may be used as a scaffold by coupling the fusion proteins to improve the induction of an immune response. The carrier protein may be any conventional carrier including any protein suitable for presenting immunogenic determinants. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Immunization of the animal may be carried out with adjuvants and/or pharmaceutical carriers. Conventional carrier proteins include, but are not limited to, keyhole limpet hemocyanin, serum proteins such as transferrin, bovine serum albumin, or human serum albumin, an ovalbumin, immunoglobulins, or hormones, such as insulin. The carrier may be present together with an adjuvant. Vaccine compositions are useful for prophylactic and therapeutic use, including stimulating an immune response in a subject. The vaccine composition disclosed herein does not induce any systemic or local toxicity reactions or any other side effects.

Adjuvants may be included in the vaccine composition to enhance the specific immune response. Thus, it is particularly important to identify an adjuvant that when combined with the antigen(s)/nucleic acid constructs and/or delivery vehicles (any of which may also be referred to as immunogenic determinant), results in a vaccine composition capable of inducing a strong specific immunological response. The immunogenic determinant may also be mixed with two or more different adjuvants prior to immunization. A large number of adjuvants have been described and used for the generation of antibodies in laboratory animals, such as mouse, rats and rabbits. In such setting the tolerance of side effect is rather high as the main aim is to obtain a strong antibody response. For use and for approval for use in pharmaceuticals, and especially for use in humans it is required that the components of the vaccine composition, including the adjuvant, are well characterized. It is further required that the composition has minimal risk of any adverse effects. In one embodiment, a vaccine composition comprises an adjuvant. In a preferred embodiment the vaccine composition is suitable for administration to a mammal, and most preferably to a human subject. The choice of adjuvant may further be selected by its ability to stimulate the type of immune response desired, B-cell or/and T-cell activation and the vaccine composition may be formulated to optimize distribution and presentation to the relevant lymphatic tissues.

Lipopolysaccharide and its various derivatives, including lipid A, have been found to be powerful adjuvants in combination with liposomes or other lipid emulsions. Freund's Complete Adjuvant is the standard in most experimental studies. Mineral oil may be added to the immunogenic composition in order to protect the antigen from rapid catabolism. Many other types of materials can be used as adjuvants in immunogenic compositions include plant products such as saponin, animal products such as chitin and numerous synthetic chemicals.

Immunogenic compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with non-specific serum albumin are exemplary appropriate diluents.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

5.4 Dosage

Vaccine compositions disclosed herein are typically administered to a subject in an amount sufficient to provide a benefit to the subject. This amount is defined as a "therapeutically effective amount." The therapeutically effective amount will be determined by the efficacy or potency of the particular composition, the duration or frequency of administration, and the size and condition of the subject, including that subject's particular treatment response. Additionally, the route of administration should be considered when determining the therapeutically effective amount. It is anticipated that the therapeutically effective amount of a vaccine composition will range from about 0.1 µg/kg to 1 mg/kg of total nucleic acid. Suitable doses include from about 5 µg/kg-500 mg/kg of total DNA, 10 µg/kg-250 µg/kg of total DNA, or 10 µg/kg-170 µg/kg of total DNA. In one embodiment, a human subject (18-50 years of age, 45-75 kg) is administered 1.2 mg-7.2 mg of DNA. "Total DNA" and 'total nucleic acid" refers to a pool of nucleic acids encoding distinct immunogenic molecules. For example, a dose of 50 mg of total DNA encoding 5 different immunogenic molecules can have 1 mg of each molecule. The vaccines may be administered multiple times, such as between about 2-6 times. In an exemplary method, 100 µg of a DNA composition is administered to a human subject at 0, 4, and 12 weeks (100 µg per administration). The therapeutically effective amount of a vaccine composition will range from about 0.1 µg/kg to 1 mg/kg of fusion protein. Suitable doses include from about 5 µg/kg-500 mg/kg of fusion protein, 10 µg/kg-250 µg/kg of fusion protein, or 10 µg/kg-170 µg/kg of fusion protein. In one embodiment, a human subject (18-50 years of age, 45-75 kg) is administered 1.2 mg-7.2 mg of fusion protein. Human vaccines are typically administered in a dosage volume of about 0.5 ml, although a half dose (i.e. about 0.25 ml) may be administered to children.

The treatments of the present application may include various 'unit doses.' A unit dose is defined as containing a predetermined-quantity of the therapeutic composition of the present application. The quantity to be administered, and the particular route and formulation, are within the skill of those in the clinical arts. A unit dose need not be administered as a single injection but may comprise continuous infusion over a set period of time. A unit dose may contain at least 0.01, 0.05, 0.1, 0.5, 1.0, 2.5, 5.0, 10.0, 15.0, 25.0 or 50.0 mg of the active ingredient. Optionally, a unit dose contains less than 0.01, 0.05, 0.1, 0.5, 1.0, 2.5, 5.0, 10.0, 15.0, 25.0 or 50.0 mg of the active ingredient. In at least one embodiment, a unit dose contains from about 0.001 mg to about 50 mg of the active ingredient. In one or more embodiments, a unit dose contains from about 1 mg to about 10 mg of active ingredient.

5.5 Administration

Vaccine compositions may be administered to a subject in therapeutically effective amounts. The effective amount may vary according to a variety of factors such as the subject's condition, weight, sex and age. Other factors include the mode of administration. The pharmaceutical or veterinary compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. Also provided are suitable topical, oral, systemic and parenteral pharmaceutical formulations for use in the methods of prophylaxis and treatment with the vaccine composition.

For example, the vaccine compositions can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the vaccine, comprising any of the herein described compounds can be employed as a prophylactic or therapeutic agent. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

Preferred modes of administration of the vaccine composition include, but are not limited to systemic administration, such as intravenous or subcutaneous administration, intradermal administration, intramuscular administration, intranasal administration, oral administration, rectal administration, vaginal administration, pulmonary administration and generally any form of mucosal administration.

A vaccine described herein can be administered once, two, three, four, five or more times. Administering the vaccine more than once has the effect of boosting the resulting immune response. The vaccine can be further boosted by administering the vaccine in a form different from the previous administration. The booster shot is either a homologous or a heterologous booster shot. A homologous booster shot is a where the first and subsequent vaccinations comprise the same constructs, fusion proteins, and more specifically the same delivery vehicle. A heterologous booster shot is where identical constructs or fusion proteins are comprised within different vectors.

A preferred recipient of the vaccine is a mammal and the mammal is in a more preferred embodiment, the subject is selected from the group of: cows, pigs, horses, sheep, goats, llamas, mice, rats, monkeys, dogs, cats and humans.

In one embodiment, the vaccine composition further comprises a second active ingredient. The second active ingredient is antibiotics, chemotherapeutics, anti-allergenics, cytokines, complement factors and co-stimulatory molecules of the immune system.

5.6 Methods of Treatment and Prevention

Also disclosed is a method for inducing an immune response in a subject, comprising administering to the subject, a vaccine described herein. The immune response includes the following types of responses: an MHC-I dependent response, an MHC-I and/or MHC-II dependent response, a T-cell dependent response, a CD4 T-cell dependent response, a $CD^{4+}$ T cell independent response, a $CD8^+$ T-cell dependent response and a B cell dependent immune response. The method is used for genetic immunization of an animal, or to treat a clinical condition in a subject in need thereof.

As discussed herein, 'treatment' includes both therapeutic treatment and prophylactic or preventative treatment, wherein the object is to prevent or slow down the targeted pathologic condition or disorder. Those in need of treatment include those already with the disorder as well as those prone to have the disorder or those in whom the disorder is to be prevented. The terms 'therapy', 'therapeutic', 'treatment' or 'treating' include the ability or action of reducing, alleviating or inhibiting or eliminating the symptoms or progress of a disease. Desirable effects of treatment include preventing occurrence or recurrence of disease, alleviation of symptoms, diminishment of direct or indirect pathological consequences of the disease, preventing metastasis, decreasing the rate of disease progression, amelioration or palliation of the disease state, and remission or improved prognosis. In some embodiments, methods and compositions of the present application are used to delay development of a disease or disorder or to slow the progression of a disease or disorder.

Treatment in accordance with the present application can include a method of treating a cancer or other neoplastic disorder which comprises administering to a patient in need of treatment a peptide, nucleic acid, antibody composition of the present application. In at least one embodiment, the treatment further comprises administering to said patient a chemotherapeutic drug, such as a drug in prodrug form. The two components may be administered together, for example in the form of a combined pill, or separately. Administration may also be sequential or simultaneous. 'Sequential' administration indicates that the components are administered at different times or time points, which may nonetheless be overlapping. Simultaneous administration indicates that the components are administered at the same time.

An effective amount, or preferably a therapeutically effective amount of the treatment of the present application is administered. An "effective amount" refers to an amount effective, at dosages and for periods of time necessary, to achieve the desired therapeutic or prophylactic result. The effective amount may vary according to the drug or prodrug with which the treatment is co-administered. A "therapeutically effective amount" of a treatment of the present application may vary according to factors such as the disease state, age, sex, and weight of the individual, and the ability of the protein, to elicit a desired therapeutic result. A therapeutically effective amount encompasses an amount in which any toxic or detrimental effects of the protein are outweighed by the therapeutically beneficial effects. A therapeutically effective amount also encompasses an amount sufficient to confer benefit, e.g., clinical benefit.

The invention also provides a method for raising an immune response in a mammal comprising the step of administering an effective amount of a composition of the invention. The immune response is preferably protective and preferably involves antibodies and/or cell-mediated immunity. The method may raise a booster response.

The invention also provides a polypeptide of the invention for use as a medicament e.g. for use in raising an immune response in a mammal.

The invention also provides the use of a polypeptide of the invention in the manufacture of a medicament for raising an immune response in a mammal.

The invention also provides a delivery device pre-filled with an immunogenic composition of the invention.

By raising an immune response in the mammal by these uses and methods, the mammal can be protected against latent viral infections including HIV, Shingles and herpes.

The mammal is preferably a human, but may be e.g. a cow, a pig, a chicken, a cat or a dog, as *E. coli* disease is also problematic in these species. Where the vaccine is for prophylactic use, the human is preferably a child (e.g. a toddler or infant) or a teenager, where the vaccine is for therapeutic use, the human is preferably a teenager or an adult. A vaccine intended for children may also be administered to adults e.g. to assess safety, dosage, immunogenicity, etc. Vaccines of the invention may be used to treat both children and adults. Thus a human patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

One way of checking efficacy of therapeutic treatment involves monitoring *E. coli* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the antigens in the compositions of the invention after administration of the composition. Typically, antigen-specific serum antibody responses are determined post-immunisation but pre-challenge whereas antigen-specific mucosal antibody responses are determined post-immunisation and post-challenge.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

Also disclosed is a method to stimulate growth of Human T Cells by treating with an alpha virus surface membrane glycoprotein Also disclosed is a method to excite Human hemopoietic cells by treating with an alpha virus surface membrane glycoprotein (including T Cells, NK cells, B Cells, dendritic cells, regulatory T Cells, macrophages, erythrocytes and all others).

Also disclosed is a method to release T Cells from anergy by treating with an alpha virus surface membrane glycoprotein.

Also disclosed is a method to overcome Breakpoint Inhibition of T Cells by treating with an alpha virus surface membrane glycoprotein.

Also disclosed is a method to treat cancer by treating with an alpha virus surface membrane glycoprotein.

5.6.1. Combination Therapy

In certain embodiments, the fusion protein can be used in combination therapy with at least one other therapeutic agent. The fusion protein and the therapeutic agent can act additively or, more preferably, synergistically. In a preferred embodiment, a composition comprising a fusion protein is administered concurrently with the administration of another therapeutic agent, which can be part of the same composition as the fusion protein or different composition. In another embodiment, a composition comprising a fusion protein is administered prior or subsequent to administration of another therapeutic agent. As many of the disorders for which the fusion protein are useful in treating are chronic disorders, in one embodiment combination therapy involves alternating between administering a composition comprising a fusion protein and a composition comprising another therapeutic agent, e.g., to minimize the toxicity associated with a particular drug. The duration of administration of each drug or therapeutic agent can be, e.g., one month, three months, six months, or a year. In certain embodiments, when a fusion protein is administered concurrently with another therapeutic agent that potentially produces adverse side effects including but not limited to toxicity, the therapeutic agent can advantageously be administered at a dose that falls below the threshold at which the adverse side is elicited.

In certain embodiment, the fusion protein is administered with a check point therapy or chemotherapy. In certain embodiment, the fusion protein is administered with antibodies to CTLA4, PD1 or PDL1.

The present fusion protein can be administered together with treatment with irradiation or one or more chemotherapeutic agents. For irradiation treatment, the irradiation can be gamma rays or X-rays. For a general overview of radiation therapy, see Hellman, Chapter 12: Principles of Radiation Therapy Cancer, in: Principles and Practice of Oncology, DeVita et al., eds., 2.nd. Ed., J. B. Lippencott Company, Philadelphia. Useful chemotherapeutic agents include methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a specific embodiment, a composition comprising the fusion protein further comprises one or more chemotherapeutic agents and/or is administered concurrently with radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three months), subsequent to administration of a composition comprising the fusion protein.

Any therapy (e.g., therapeutic or prophylactic agent) which is useful, has been used, or is currently being used for the prevention, treatment, and/or management of a disorder, e.g., cancer, can be used in compositions and methods of the invention. Therapies (e.g., therapeutic or prophylactic agents) include, but are not limited to, peptides, polypeptides, conjugates, nucleic acid molecules, small molecules, mimetic agents, synthetic drugs, inorganic molecules, and organic molecules. Non-limiting examples of cancer therapies include chemotherapies, radiation therapies, hormonal therapies, and/or biological therapies/immunotherapies and surgery. In certain embodiments, a prophylactically and/or therapeutically effective regimen of the invention comprises the administration of a combination of therapies.

Examples of cancer therapies include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; Bcl-2 inhibitors; Bcl-2 family inhibitors, including ABT-737; BCR/ABL antagonists; benzochlorins; benzoylstaurosporine; beta lactam derivatives; betaalethine; betaclamycin B; betulinic acid; bFGF inhibitor, bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor, cytostatin; daclizimab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor, multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor, platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor, retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor, stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor, translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor, urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

In some embodiments, the therapy(ies) used in combination with the fusion protein is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide). In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent.

In some embodiments, the therapy(ies) used in combination with fusion protein is an anti-angiogenic agent. Non-limiting examples of anti-angiogenic agents include proteins, polypeptides, peptides, conjugates, antibodies (e.g., human, humanized, chimeric, monoclonal, polyclonal, Fvs, ScFvs, Fab fragments, F(ab)2 fragments, and antigen-binding fragments thereof) such as antibodies that bind to TNF-alpha, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publ'n No. 2005/0002934 A1 at paragraphs 277-282, which is incorporated by reference in its entirety. In other embodiments, the therapy(ies) used in accordance with the invention is not an anti-angiogenic agent.

In some embodiments, the therapy(ies) used in combination with the fusion protein is an inflammatory agent. Non-limiting examples of anti-inflammatory agents include any anti-inflammatory agent, including agents useful in therapies for inflammatory disorders, well-known to one of skill in the art. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT.™.)), β2-agonists (e.g., abuterol (VENTOLIN.™. and PROVENTIL.™.), bitolterol (TORNALATE.™.), levalbuterol (XOPONEX.™.), metaproterenol (ALUPENT.™.), pirbuterol (MAXAIR.™.), terbutlaine (BRETHAIRE.™. and BRETHINE.™.), albuterol (PROVENTIL.™., REPETABS.™., and VOLMAX.™.), formoterol (FORADIL AEROLIZER.™.), and salmeterol (SEREVENT.™. and SEREVENT DISKUS.™.)), and methylxanthines (e.g., theophylline (UNIPHYL.™., THEO-DUR.™., SLO-BID.™., AND TEHO-42.™.)). Examples of NSAIDs include, but are not limited to, aspirin, ibuprofen, celecoxib (CELEBREX™), diclofenac (VOLTAREN.™.), etodolac (LODINE.™.), fenoprofen (NALFON.™.), indomethacin (INDOCIN.™.), ketoralac (TORADOL.™.), oxaprozin (DAYPRO.™.), nabumentone (RELAFEN.™.), sulindac (CLINORIL.™.), tolmentin (TOLECTIN.™.), rofecoxib (VIOXX.™.), naproxen (ALEVE.™., NAPROSYN.™.), ketoprofen (ACTRON.™.) and nabumetone (RELAFEN.™.). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON.™.), corticosteroids (e.g., methylprednisolone (MEDROL.™.)), cortisone, hydrocortisone, prednisone (PREDNISONE.™. and DELTASONE.™.), prednisolone (PRELONE.™. and PEDIAPRED.™.), triamcinolone, azulfidine, and inhibitors of eicosanoids (e.g., prostaglandins, thromboxanes, and leukotrienes. In other embodiments, the therapy(ies) used in accordance with the invention is not an anti-inflammatory agent.

In certain embodiments, the therapy(ies) used is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, chlorambucil, cyclophosphamide, ifosfamide, decarbazine, mechlorethamine, melphalan, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclines include but are not limited to daunorubicin, doxorubicin, epirubicin, idarubicin, and mitoxantrone. Topoisomerase II inhibitors include, but are not limited to, topotecan, irinotecan, etoposide (VP-16), and teniposide. Mitotic inhibitors include, but are not limited to taxanes (paclitaxel, docetaxel), and the *vinca* alkaloids (vinblastine, vincristine, and vinorelbine).

In some embodiments, the fusion protein is used in combination with radiation therapy comprising the use of x-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

5.7. Types of Cancer

Any type of cancer can be prevented, treated, and/or managed in accordance with the invention. Non-limiting examples of cancers that can be prevented, treated, and/or managed in accordance with the invention include: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; dendritic cell cancer, including plasmacytoid dendritic cell cancer, NK blastic lymphoma (also known as cutaneous NK/T-cell lymphoma and agranular (CD4+/CD56+) dermatologic neoplasms); basophilic leukemia; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer, pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor, bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

The prophylactically and/or therapeutically effective regimens are also useful in the treatment, prevention and/or management of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. In some embodiments, cancers associated with aberrations in apoptosis are prevented, treated and/or managed in accordance with the methods of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are prevented, treated and/or managed in accordance with the methods of the invention. In other specific embodiments, a sarcoma, melanoma, or leukemia is prevented, treated and/or managed in accordance with the methods of the invention. In certain embodiments, the subjects have acute myelogenous leukemia (AML). In certain other embodiments, the subjects have myelodysplastic syndrome (MDS). In other embodiments, the subjects have chronic myelomonocytic leukemia (CMML). In other specific embodiments, myelodysplastic syndrome is prevented, treated and/or managed in accordance with the methods of the invention.

A major objective in treatment of cancers is to be able to target the tumor with sufficient levels of the appropriate therapeutic without systemic toxicity.

In certain embodiments, the method of treating cancer includes: (i) a reduction of cancer cells, (ii) absence of increase of cancer cells; (iii) a decrease in viability of cancer cells; (iv) decrease in growth of cancer cells, in a subject.

In certain embodiments, the subject that is treated with the present method of the disclosure has been diagnosed with the disease and has undergone therapy. In certain embodiments, the subject that is treated with the present method of the disclosure has been diagnosed with cancer and has undergone cancer therapy.

In certain embodiments, the subject is in remission from cancer. In certain embodiments, the subject has relapsed from cancer. In certain embodiments, the subject has failed cancer treatment.

5.8 Kits

Provided herein are articles of manufacture and kits containing materials useful for treating the conditions described herein. The article of manufacture may include a container of a compound as described herein with a label. Suitable containers include, for example, bottles, vials, and test tubes. The containers may be formed from a variety of materials such as glass or plastic. The container holds a composition having a vaccine which is effective for treating or preventing cancer. The label on the container may indicate that the composition is useful for treating specific conditions and may also indicate directions for administration.

In one or more embodiments, the present invention can provide for a kit comprising a therapeutically effective amount of vaccine. It is to be understood that any of the embodiments of the vaccine can be included in one or more kits in accordance with one or more implementations of the present disclosure.

5.9 Immune Response

Comparison of the immune response raised in a subject by the polypeptide with the immune response raised by the full length protein may be carried out by any means available to one of skill in the art. One simple method as used in the examples below involves immunization of a model subject such as mouse and then challenge with a lethal dose of *E. coli*. For proper comparison, one of skill in the art would naturally select the same adjuvant such as Freund's complete adjuvant. In such a test the immunogenic polypeptide fragments of the present invention will raise a substantially similar immune response in a subject (i.e., will provide substantially the same protection against the lethal challenge) if, for example, the polypeptide provides at least 70% of the protection provided by the full length protein, at least 80% of the protection provided by the full length protein, at least 85% of the protection provided by the full length protein, at least 90% of the protection provided by the full length protein, at least 95% of the protection provided by the full length protein, at least 97% of the protection provided by the full length protein, at least 98% of the protection provided by the full length protein, or at least 99% of the protection provided by the full length protein.

The compositions of the invention may elicit both a cell mediated immune response as well as a humoral immune response. This immune response will preferably induce long lasting (e.g. neutralising) antibodies and a cell mediated immunity that can quickly respond upon reexposure to the antigen.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class 1 molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines.

These secreted cytokines can activate B cells, cytotoxic T cells, macrophages, and other cells that participate in an immune response.

6. EXAMPLES

6.1 Generation of Fusion proteins

In one embodiment, Sindbis fusion protein is generated by baculovirus expression in Sf9 insect cells. Since baculoviruses can only infect specific invertebrate species, they are nonpathogenic to mammals. Unlike bacterial protein expression, proteins expressed in the baculovirus system are processed, folded, and modified similarly to those produced in a mammalian expression system. Additionally, baculovirus-expressed proteins are easily scaled up to produce large quantities of recombinant protein. Insect cell lines are available that grow well in suspension cultures, allowing the production of recombinant proteins in large-scale bioreactors. While both insect and mammalian cells are capable of making N-linked glcosylations, the specific glycosylation pathway is different. N-glycans produced in insect cells can have either a high-mannose or paucimannosidic structure, both of which have terminal mannose residues. N-glycans produced in mammalian cells can have either a high-mannose structure or a complex structure terminating in galactose and sialic acid. Binding of SINV to the dendritic cell ("DC") receptor (Dendritic Cell-Specific Intercellular adhesion molecule-3-Grabbing Non-integrin) DC-SIGN requires high mannose glycosylation of its envelope glycoproteins. Virus produced in mammalian cells will not bind DC-SIGN without additional enzymatic modifications. Therefore, production of fusion protein in insect cells achieves efficient targeting of the TAA to the DC.

The gene encoding the VGP is produced through gene synthesis and codon-optimized for insect cell expression. The recombinant fusion protein is composed of the ectodomains of the pE2 and E1 Sindbis glycoproteins connected by a flexible linker and linked to a TAA by a second linker (see FIG. 4). In one embodiment, TAA is NY-ESO-1. In certain embodiment, other TAAs are inserted into the coding sequence. Alternatively, a construct is generated with two or more TAAs in tandem, which results in a more potent immune response. The E3 component of pE2 acts as a signal peptide for secretion of the protein, assists in the binding of E1 and E2, and is naturally cleaved from the mature protein by furin. Alphavirus glycoproteins are produced as the mature secreted protein forming a trimer of the heterodimeric complex of E2 and E1, which mimic the trimeric glycoprotein spike observed on the SINV envelope. The second flexible linker allows proper folding of NY-ESO-1 without interfering with the multimerization of E2/E1. Additionally, since the first 80 amino acids of NY-ESO-1 are glycine-rich and largely devoid of T cell antigens, in one embodiment, only amino acids residues 81-180 have been included in the construct. In certain embodiments, the TAA comprises amino acid residues 1-180, 81-100, 100-150, 150-180 of NY-ESO-1. A His-tag has been added to the C-terminus of the protein for purification purposes. The novel protein is analyzed to determine its multimeric structure by non-denaturing gel and size-exclusion chromatography. Further, ELISA and western blot assays specific for the protein are developed. The protein has several antigenic targets (NY-ESO-1, His-tag, and SINV E1 and E2) that are detected with commercial antibodies.

Provided herewith is a viral glycoprotein complex which is a recombinant protein consisting of the ectodomains E3, E2, and E1 proteins of the Sindbis virus linked to a truncated peptide derived from the tumor-associated antigen NY-ESO-1. The amino acid sequences for the Sindbis virus structural proteins E3, E2, 6K, and E1 (NCBI website reference sequence NP_062890.1). Transmembrane domains of E2 and E1 proteins were removed from the coding sequence. The E2 and E1 proteins were joined by a flexible glycine/serine linker (GGGGSGGGGSGGGGSGGGG)(SEQ ID NO: 13) in place of the 6K region. The amino acid sequence for NY-ESO-1 (NCBI website reference sequence NP_001318.1). As N-terminus of NY-ESO-1 is very glycine-rich and largely devoid of T cell antigens, in one embodiment, the first 78 amino acids of the protein were deleted. In one embodiment, the Sindbis E3/E2/E1 sequence was linked to the truncated 102 amino acid NY-ESO-1 protein by a TEV cleavage site (ENLYFQ)(SEQ ID NO: 14) and a second glycine/serine linker (GGGGSGGGGSGGGGS)(SEQ ID NO: 15). In one embodiment, a 6×-His tag was added to the C-terminus of the recombinant protein for purification purposes. The DNA sequence encoding the recombinant protein was synthesized by Genscript (Piscataway, N.J.) and codon optimized for expression in Sf9 cells. The DH10Bac strain was used for recombinant bacmid generation. Sf9 insect cells were transfected with bacmid using Cellfectin II and incubated in Sf-900 II medium for 5-7 days at 27° C. The supernatant after centrifugation was collected and designated as P1 viral stock. Cells were further infected with P1 to generate high titer P2 stock. Sf9 cells were transfected with P2 virus and media was collected 72 hours later. Supernatant was dialyzed against 50 mM Tris, 150 mM NaCl, pH8.0 containing protease inhibitor, and protein was purified with a Ni column and analyzed by anti-His western blot.

6.2 Receptor Binding Analysis

SINV binds to receptors on both tumor cells (laminin receptor) and dendritic cells (DC-SIGN). The fusion protein, maintaining the conformational shape of the E2/E1 heterodimeric trimer on the surface of the virus, binds to these same receptors. For DC-SIGN binding, an assay using protein A microbeads and DC-SIGN Fc fusion protein are used. Fusion protein binds to beads maximally coated with DC-SIGN, then a fluorescently labelled secondary antibody for the VGP (anti-His or anti-NY-ESO-1) is used for detection by flow cytometry. Binding is analyzed at multiple protein concentrations and comparing to other DC-SIGN-targeting methods such as anti-DC-SIGN antibodies. Using a flow cytometer equipped with a 96-well plate reader, these assays can be performed in high throughput fashion. Viral proteins target antigens to DC with similar affinity to antibodies for DC-SIGN. Additionally, binding of the fusion protein to DC is analyzed from both humans (expressing DC-SIGN) and mouse (L-SIGN). Receptor-blocking antibodies and mannan, a mannose polysaccharide, are used to demonstrate the specificity of the interaction. For laminin receptor binding, the binding is analyzed using multiple tumor cell lines with varying degrees of laminin receptor expression. This binding can be blocked using an antibody to the laminin receptor or with excess laminin, the natural ligand for the receptor. The fusion protein preferentially binds these cells over bystander cells and effectively delivers a tumor-associated antigen to DC for processing and presentation.

6.3 In Vitro Assays

SINV boosts the immune system's response to tumor cells through NK cell recruitment and activation of T cells against tumor associated antigens encoded by the virus. The latter of these effects is accomplished by delivery of antigen to DC by the virus through the DC-SIGN receptor. In order to induce a strong T cell response, the DC must first become activated through the detection of pathogen-associated molecular patterns (PAMPs) that are common among viruses, bacteria, or parasites. Activated DC express increased levels of MHC molecules as well as the costimulatory molecules B7-1 and B7-2. It is therefore necessary to assess whether the recombinant fusion protein has sufficient immunogenicity to induce DC activation or if it is necessary to couple it to an adjuvant.

From human peripheral blood mononuclear cells (PBMC), pure populations of specific immune cell types are obtained by magnetic bead selection, then the direct effect that the VGP/NY-ESO-1 is evaluated. Activation of DC and NK cells can be measured by flow cytometric analysis of activation markers on the cell surface and the detection of cytokine secretion by ELISA. The ability to modulate a tumor-specific response is assessed using T cells obtained from cancer patients. These patients have been exposed to the tumor antigen and have an elevated percentage of tumor-specific T cells compared to healthy donors. DC from the patient is treated with the recombinant fusion protein overnight, during which time, the protein is absorbed, processed, and relevant epitopes are presented on the cell surface. DC is co-cultured with patient T cells for several days, at which point the T cells will be analyzed for an antigen-specific response. Using CFSE-labeled T cells, T cell proliferation is measured by flow cytometry. An ELISPOT assay is used to detect activated NY-ESO-I-specific T cells. NY-ESO-1-specific T cells produce IFNγ upon recognition of their specific epitope presented by the DC, which are captured for detection by antibodies coating the wells of the ELISPOT plate. These assays demonstrates that peptides from the fusion protein are processed and presented by the dendritic cells and T cell response is stimulated in humans.

While we believe that the most important effect of the VGP treatment is through activation of the immune system, the role of direct tumor targeting through the laminin receptor should not be discounted. SINV induces apoptosis in tumor cells upon entry and in the absence of viral replication. The effects the VGP has on tumor cell growth and survival is investigated in vitro. Several tumor cell lines with varying levels of laminin receptor expression is used to evaluate what role if any direct protein-tumor interaction has on the efficacy of the treatment.

6.4 In Vivo Stimulation Assays

Before attempting to treat an actively growing tumor, it is important to demonstrate induction of a tumor-specific immune response in vivo with VGP/NY-ESO-1. Normal mice have not encountered NY-ESO-1 and it is recognized by the immune system as a foreign antigen. Immunization of mice with the VGP/NY-ESO-1 by ip injection results in activation and proliferation of NY-ESO-I-specific T cells as well as fusion protein-specific T cells as well as NK cell activation. To establish efficacy of this treatment, VGP/NY-ESO-1 shows greater immunogenicity than the VGP alone, NY-ESO-1 alone, and anti-DC-SIGN/NY-ESO-1 (controls). The checkpoint inhibitors anti-CTLA-4 and PD-1 shows strong immunotherapeutic potential and works synergistically with the disclosed therapy for an even stronger immune response. The effects of the presently disclosed treatment with and without co-administration of these blocking antibodies is evaluated.

Based on known MHC binding preferences, epitopes from NY-ESO-1 and the VGP are presented by the MHC molecules of a particular mouse strain. Alternatively, trangenic mice expressing human MHC molecules, for which NY-ESO-1 epitopes are known, can be used. Samples from blood, spleen, and draining lymph nodes are taken to check for immune stimulation. MHC tetramer staining are used to verify the presence of an expanded population of NY-ESO-1 and VGP-specific T cells. These cells exist in naïve mice but in minute amounts below the detection threshold. In a successful immunization, these cells proliferate and are readily detectable by flow cytometry. Additionally, flow cytometry is used to analyze the activation state of these tetramer+ cells, by looking at surface markers such as CD62L and CD69, which are present only on naïve and activated cells, respectively. While activation of VGP-specific T cells is considered an off-target effect, it further improves the immune response to the tumor, as these antigens would also be targeted to the tumor itself.

ELISPOT assays are used to determine that these NY-ESO-1-specific T cells have effector function. CD8+ T cells harvested from the spleen and lymph nodes of immunized mice are co-cultured with antigen-presenting cells preloaded with NY-ESO-1. Activated T cells specific for these epitopes produce cytokines such as IFNγ in response, which are captured by antibodies coating the bottom of the well for detection. The effector function of these activated T cells is analyzed by performing a cytotoxicity assay. Similar to the ELISPOT assay, CD8+ T cells from immunized mice are co-cultured with antigen presenting cells preloaded with relevant peptides. Alternatively, a syngeneic murine cell line transduced with lentivirus to express NY-ESO-1 is used. Activated CD8+ CTL directly kill these NY-ESO-1-presenting cells, and the cytotoxicity is measured by detection of intracellular proteins from the lysed cells such as lactate dehydrogenase in the supernatant.

The effect of the therapy on other immune cell populations is analysed, which can be accomplished by flow cytometry. Specifically, the effects of the treatment on the percentage of several immune cell types (CD4+ and CD8+ T cells, DC, NK cells, B cells, macrophages) with respect to one another, as well as the total cell number are analysed. Antibodies generated by the mouse against the recombinant protein is evaluated by analyzing blood serum. Plasma cells generate antibodies specific for NY-ESO-1 and the VGP. In certain embodiments, when multiple doses are adminstered, these antibodies may interfere with the effectiveness of the therapy. In certain embodiments, the antibodies aid in tumor clearance as these antigens are targeted to the tumor itself, making it more antigenic.

The proper dosing strategy (amount of protein, number of doses, frequency of doses) is examined to generate a strong anti-tumor immune response before proceeding into a tumor model. Additionally, ELISA is developed to detect the VGP in mouse serum and tissues to evaluate dosing as well as protein trafficking and stability in vivo.

In order to properly activate T cells, DC are activated through the detection of pathogen associated molecular patterns (PAMPs). In certain embodiments, VGP/NY-ESO-1 is coupled with an adjuvant to increase its immunogenicity.

LIST OF REFERENCES

1. Siegel R, Naishadham D, & Jemal A (2013) Cancer statistics, 2013. CA Cancer J Clin 63(1):11-30.
2. Schwab C L, English D P, Roque D M, Pasternak M, & Santin A D (2014) Past, present and future targets for immunotherapy in ovarian cancer. Immunotherapy 6(12):1279-1293.
3. Zhang L, Conejo-Garcia J R, Katsaros D, Gimotty P A, Massobrio M, Regnani G, Makrigiannakis A, Gray H, Schlienger K, Liebman M N, Rubin S C, & Coukos G (2003) Intratumoral T cells, recurrence, and survival in epithelial ovarian cancer. N Engl J Med 348(3):203-213.
4. Dunn G P, Bruce A T, Ikeda H, Old L J, & Schreiber R D (2002) Cancer immunoediting: from immunosurveillance to tumor escape. Nature immunology 3(11):991-998.
5. Gill S, Maus M V, & Porter D L (2015) Chimeric antigen receptor T cell therapy: 25 years in the making. Blood Rev.
6. Maude S L, Barrett D, Teachey D T, & Grupp S A (2014) Managing cytokine release syndrome associated with novel T cell-engaging therapies. Cancer J 20(2):119-122.
7. Li L, Jose J, Xiang Y, Kuhn R J, & Rossmann M G (2010) Structural changes of envelope proteins during alphavirus fusion. Nature 468(7324):705-708.
8. Knight R L, Schultz K L W, Kent R J, Venkatesan M, & Griffin D E (2009) Role of N-Linked Glycosylation for Sindbis Virus Infection and Replication in Vertebrate and Invertebrate Systems. Journal of virology 83(11):5640-5647.
9. Cheever M A, Allison J P, Ferris A S, Finn O J, Hastings B M, Hecht T T, Mellman I, Prindiville S A, Viner J L, Weiner L M, & Matrisian L M (2009) The prioritization of cancer antigens: a national cancer institute pilot project for the acceleration of translational research. Clinical cancer research: an official journal of the American Association for Cancer Research 15(17):5323-5337.
10. Kost T A, Condreay J P, & Jarvis D L (2005) Baculovirus as versatile vectors for protein expression in insect and mammalian cells. Nature biotechnology 23(5):567-575.
11. Morizono K, Ku A, Xie Y, Harui A, Kung S K, Roth M D, Lee B, & Chen I S (2010) Redirecting lentiviral vectors pseudotyped with Sindbis virus-derived envelope proteins to DC-SIGN by modification of N-linked glycans of envelope proteins. Journal of virology 84(14):6923-6934.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, and publications are cited throughout this application, the disclosures of which, particularly, including all disclosed chemical structures, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

We claim:

1. An isolated or recombinant fusion protein comprising alpha virus surface membrane glycoproteins E1, E2, a linker and at least one tumor associated antigen, wherein the fusion protein comprises: (i) an amino acid sequence having at least 98% identity to SEQ ID NO:1, or (ii) at least amino acid residues at positions 66-978 of SEQ ID NO:1.

2. The fusion protein of claim 1, wherein the fusion protein comprises an amino acid sequence having at least 98% identity to SEQ ID NO: 1, and wherein the fusion protein further comprises a deletion of amino acid residues at positions 979-984 of SEQ ID NO:1.

3. The fusion protein of claim 1 encoded by a nucleic acid molecule having at least 95% identity to SEQ ID NO: 2.

4. A vaccine comprising the fusion protein of claim 1, wherein the fusion protein is capable of eliciting an immune response comprising T-cells in a subject.

5. The fusion protein of claim 1, wherein the fusion protein further comprises a tumor associated antigen that is a polypeptide fragment of a protein selected from a group consisting of WT1, MUC1, LMP2, HPV E6 E7, EGFRvIII, HER-2/neu, MAGE A3 , p53nonmutant, NY-ESO1, PSMA, GD2, CEA, MelanA/MART, Ras mutant, gp100, p53 nonmutant, Proteinase3 (PR1), Bcr-abl fusion, Tyrosinase, Survivin, PSA, hTERT, EphA2, PAP, ML-IAP, AFP, EpCAM, ERG (TMPRSS2/ERG fusion), NA17, PAX3, ALK, Androgen receptor, Cyclin B1, MYCN, RhoC, TRP-2, GD3, Fucosyl GM1, Mesothelin, PSCA, MAGE A1, CYPIB1, PLAC1, GM3, BORIS, Tn, GloboH, EVT6-AML, NY-BR-1, RGS5, SART3, Carbonic anhydrase IX, PAX5, OY-TES1, Sperm protein 17, LCK, HMWMAA, AKAP-4, SSX2, XAGE 1, Legumain, Tie 2, Page4, VEGFR2, MAD-CT-1, FAP, PDGRFR-β, MAD-CT-2, and Fos-related antigen 1.

6. A method to produce a fusion protein comprising expressing the fusion protein from an expression vector comprising a nucleotide construct encoding: (a) alpha virus surface membrane glycoprotein E1 and E2; (b) at least one tumor associated antigen or viral antigen, wherein the tumor associated antigen or viral antigen is operatively linked to the alpha virus surface membrane glycoprotein E1 and E2, wherein the fusion protein comprises: (i) an amino acid sequence having at least 98% identity to SEQ ID NO:1, or (ii) at least amino acid residues at positions 66-978 of SEQ ID NO:1, and wherein the fusion protein stimulates an immune response when administered to a subject.

7. The isolated or recombinant fusion protein of claim 1, further comprising one or more glycosylation sites.

8. The isolated or recombinant fusion protein of claim 7, wherein the one or more glycosylation sites are N-linked glycosylations.

9. The isolated or recombinant fusion protein of claim 7, wherein the one or more glycosylation sites are at amino acid residues positions 261, 383, 587 or 693 of SEQ ID NO:1.

10. The fusion protein of claim 1, wherein the fusion protein further comprises a deletion of amino acid residues at (i) positions 1-65 of SEQ ID NO:1; or (ii) positions 1-65 and 979-984 of SEQ ID NO:1.

\* \* \* \* \*

SEQUENCE LISTING

```
<160> NUMBER OF SEQ ID NOS: 15

<210> SEQ ID NO 1
<211> LENGTH: 984
<212> TYPE: PRT
<213> ORGANISM: Artificial Sequence
<220> FEATURE:
<223> OTHER INFORMATION: Synthetic: E3-E2-link-E1-TEV-link-NY-ESO-1-6X
      His

<400> SEQUENCE: 1

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30
```

-continued

```
Arg Ala Leu Asp Ile Leu Glu Glu Asn Val Asn His Glu Ala Tyr Asp
             35                  40                  45
Thr Leu Leu Asn Ala Ile Leu Arg Cys Gly Ser Ser Gly Arg Ser Lys
 50                  55                  60
Arg Ser Val Ile Asp Asp Phe Thr Leu Thr Ser Pro Tyr Leu Gly Thr
 65                  70                  75                  80
Cys Ser Tyr Cys His His Thr Val Pro Cys Phe Ser Pro Val Lys Ile
                 85                  90                  95
Glu Gln Val Trp Asp Glu Ala Asp Asp Asn Thr Ile Arg Ile Gln Thr
                100                 105                 110
Ser Ala Gln Phe Gly Tyr Asp Gln Ser Gly Ala Ala Ser Ala Asn Lys
            115                 120                 125
Tyr Arg Tyr Met Ser Leu Lys Gln Asp His Thr Val Lys Glu Gly Thr
130                 135                 140
Met Asp Asp Ile Lys Ile Ser Thr Ser Gly Pro Cys Arg Arg Leu Ser
145                 150                 155                 160
Tyr Lys Gly Tyr Phe Leu Leu Ala Lys Cys Pro Pro Gly Asp Ser Val
                165                 170                 175
Thr Val Ser Ile Val Ser Ser Asn Ser Ala Thr Ser Cys Thr Leu Ala
            180                 185                 190
Arg Lys Ile Lys Pro Lys Phe Val Gly Arg Glu Lys Tyr Asp Leu Pro
        195                 200                 205
Pro Val His Gly Lys Lys Ile Pro Cys Thr Val Tyr Asp Arg Leu Lys
        210                 215                 220
Glu Thr Thr Ala Gly Tyr Ile Thr Met His Arg Pro Arg Pro His Ala
225                 230                 235                 240
Tyr Thr Ser Tyr Leu Glu Glu Ser Ser Gly Lys Val Tyr Ala Lys Pro
                245                 250                 255
Pro Ser Gly Lys Asn Ile Thr Tyr Glu Cys Lys Cys Gly Asp Tyr Lys
                260                 265                 270
Thr Gly Thr Val Ser Thr Arg Thr Glu Ile Thr Gly Cys Thr Ala Ile
            275                 280                 285
Lys Gln Cys Val Ala Tyr Lys Ser Asp Gln Thr Lys Trp Val Phe Asn
        290                 295                 300
Ser Pro Asp Leu Ile Arg His Asp Asp His Thr Ala Gln Gly Lys Leu
305                 310                 315                 320
His Leu Pro Phe Lys Leu Ile Pro Ser Thr Cys Met Val Pro Val Ala
                325                 330                 335
His Ala Pro Asn Val Ile His Gly Phe Lys His Ile Ser Leu Gln Leu
            340                 345                 350
Asp Thr Asp His Leu Thr Leu Leu Thr Thr Arg Arg Leu Gly Ala Asn
        355                 360                 365
Pro Glu Pro Thr Thr Glu Trp Ile Val Gly Lys Thr Val Arg Asn Phe
370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
                405                 410                 415
Pro His Glu Ile Val Gln His Tyr Tyr His Arg His Pro Gly Gly Gly
            420                 425                 430
Gly Ser Gly Gly Gly Gly Ser Gly Gly Gly Gly Ser Gly Gly Gly Gly
        435                 440                 445
Tyr Glu His Ala Thr Thr Val Pro Asn Val Pro Gln Ile Pro Tyr Lys
```

-continued

```
            450                 455                 460
Ala Leu Val Glu Arg Ala Gly Tyr Ala Pro Leu Asn Leu Glu Ile Thr
465                 470                 475                 480

Val Met Ser Ser Glu Val Leu Pro Ser Thr Asn Gln Glu Tyr Ile Thr
                485                 490                 495

Cys Lys Phe Thr Thr Val Val Pro Ser Pro Lys Ile Lys Cys Cys Gly
            500                 505                 510

Ser Leu Glu Cys Gln Pro Ala Ala His Ala Asp Tyr Thr Cys Lys Val
            515                 520                 525

Phe Gly Gly Val Tyr Pro Phe Met Trp Gly Ala Gln Cys Phe Cys
    530                 535                 540

Asp Ser Glu Asn Ser Gln Met Ser Glu Ala Tyr Val Glu Leu Ser Ala
545                 550                 555                 560

Asp Cys Ala Ser Asp His Ala Gln Ala Ile Lys Val His Thr Ala Ala
                565                 570                 575

Met Lys Val Gly Leu Arg Ile Val Tyr Gly Asn Thr Thr Ser Phe Leu
            580                 585                 590

Asp Val Tyr Val Asn Gly Val Thr Pro Gly Thr Ser Lys Asp Leu Lys
            595                 600                 605

Val Ile Ala Gly Pro Ile Ser Ala Ser Phe Thr Pro Phe Asp His Lys
            610                 615                 620

Val Val Ile His Arg Gly Leu Val Tyr Asn Tyr Asp Phe Pro Glu Tyr
625                 630                 635                 640

Gly Ala Met Lys Pro Gly Ala Phe Gly Asp Ile Gln Ala Thr Ser Leu
                645                 650                 655

Thr Ser Lys Asp Leu Ile Ala Ser Thr Asp Ile Arg Leu Leu Lys Pro
            660                 665                 670

Ser Ala Lys Asn Val His Val Pro Tyr Thr Gln Ala Ser Ser Gly Phe
            675                 680                 685

Glu Met Trp Lys Asn Asn Ser Gly Arg Pro Leu Gln Glu Thr Ala Pro
            690                 695                 700

Phe Gly Cys Lys Ile Ala Val Asn Pro Leu Arg Ala Val Asp Cys Ser
705                 710                 715                 720

Tyr Gly Asn Ile Pro Ile Ser Ile Asp Ile Pro Asn Ala Ala Phe Ile
                725                 730                 735

Arg Thr Ser Asp Ala Pro Leu Val Ser Thr Val Lys Cys Glu Val Ser
            740                 745                 750

Glu Cys Thr Tyr Ser Ala Asp Phe Gly Gly Met Ala Thr Leu Gln Tyr
            755                 760                 765

Val Ser Asp Arg Glu Gly Gln Cys Pro Val His Ser His Ser Ser Thr
770                 775                 780

Ala Thr Leu Gln Glu Ser Thr Val His Val Leu Glu Lys Gly Ala Val
785                 790                 795                 800

Thr Val His Phe Ser Thr Ala Ser Pro Gln Ala Asn Phe Ile Val Ser
                805                 810                 815

Leu Cys Gly Lys Lys Thr Thr Cys Asn Ala Glu Cys Lys Pro Pro Ala
            820                 825                 830

Asp His Ile Val Ser Thr Pro His Lys Asn Asp Gln Glu Phe Gln Ala
            835                 840                 845

Ala Ile Ser Lys Thr Ser Glu Asn Leu Tyr Phe Gln Gly Gly Gly Gly
            850                 855                 860

Gly Ser Gly Gly Gly Gly Ser Gly Gly Gly Gly Ser Gly Ala Arg Gly
865                 870                 875                 880
```

```
Pro Glu Ser Arg Leu Leu Glu Phe Tyr Leu Ala Met Pro Phe Ala Thr
                885                 890                 895
Pro Met Glu Ala Glu Leu Ala Arg Arg Ser Leu Ala Gln Asp Ala Pro
            900                 905                 910
Pro Leu Pro Val Pro Gly Val Leu Leu Lys Glu Phe Thr Val Ser Gly
        915                 920                 925
Asn Ile Leu Thr Ile Arg Leu Thr Ala Ala Asp His Arg Gln Leu Gln
    930                 935                 940
Leu Ser Ile Ser Ser Cys Leu Gln Gln Leu Ser Leu Leu Met Trp Ile
945                 950                 955                 960
Thr Gln Cys Phe Leu Pro Val Phe Leu Ala Gln Pro Pro Ser Gly Gln
                965                 970                 975
Arg Arg His His His His His His
            980

<210> SEQ ID NO 2
<211> LENGTH: 2952
<212> TYPE: DNA
<213> ORGANISM: Artificial sequence
<220> FEATURE:
<223> OTHER INFORMATION: Synthetic construct

<400> SEQUENCE: 2
atgtcagccg ctccactcgt cactgctatg tgcctgctcg gtaacgtcag cttcccttgc    60
gacagacccc caacttgcta cactcgtgag ccatctaggg ctctcgatat cttggaggaa   120
aacgtgaacc acgaggctta cgacaccctg ctcaacgcca tcctgagatg cggatccagc   180
ggtcgctcca agcgtagcgt gattgacgat ttcacactca cgtcgcctta cttgggtacc   240
tgctcctact gtcaccatac tgtcccgtgt ttctcacctg tcaagatcga gcaggtttgg   300
gacgaagcag acgataacac aatccgcatt cagacgagcg ctcaattcgg ttacgatcag   360
agcggcgctg cctctgctaa caaataccgt tacatgtctc tcaaacaaga ccacaccgtc   420
aaggagggca ctatggacga tatcaagatt tctacttcag gaccttgccg ccgtctgtct   480
tacaaaggtt acttcttgct ggctaagtgt cctcccggag actcagtcac agttagtatc   540
gtctcttcaa actctgcaac atcatgcacg ctggcgcgca agattaaacc aaagttcgtt   600
ggccgtgaga aatacgacct cccaccggtg cacggaaaga aatcccttg taccgtctac   660 gatcgtttga aggaaaccac tgccggctac attaccatgc acaggccaag accgcatgct   720
tacactagtt acctggaaga agttcgggc aaagtgtacg ccaagcctcc ctcgggaaag   780
aacatcacat acgagtgcaa atgtggagac tacaagaccg gtactgtcag cacaaggacg   840
gaaatcaccg gttgcactgc tattaagcag tgtgtcgcct acaaatcgga ccaaactaag   900
tgggttttca actcccccga tctgatcaga cacgacgatc atactgccca gggaaaattg   960
cacctgccgt tcaagctcat tccttcaaca tgcatggtgc ccgtcgctca tgccccaaac  1020
gtgatccacg gtttcaagca tattagtctc caattggaca cagatcacct cacgctcttg  1080
acaacgagga gattgggagc taaccctgag cccaccactg aatggatcgt gggcaagaca  1140
gtccgcaact tcacggtgga ccgtgatggc ctggagtaca tctggggaaa ccacgaacca  1200
gttcgcgtgt acgctcagga gtccgcacca ggagacccac acggttggcc acatgaaatc  1260
gtccaacatt actaccaccg tcatcctggt ggaggaggtt cgggaggagg tggatccgga  1320
ggtggcggaa gcgtggcgg aggttacgag cacgctacaa cggtgcctaa cgtcccccag  1380
atcccataca aggccttggt ggaaagagct ggatacgcac cactgaacct cgagatcacc  1440
```

```
gtgatgtcca gcgaagtcct gccaagcaca aaccaggagt acatcacgtg caagttcacc   1500
actgtggtcc catcaccgaa aattaagtgc tgtggtagtc tggaatgcca acctgcagcg   1560
cacgctgact acacttgtaa ggttttcggc ggagtgtacc ccttcatgtg gggtggcgct   1620
cagtgcttct gtgacagtga gaactcgcaa atgtccgagg cttacgttga actgtctgca   1680
gactgcgcgt cagatcacgc acaggcgatc aaagtgcata ccgctgccat gaaggttggt   1740
ttgcgcattg tgtacggcaa cacaacgtct ttcctggatg tctacgttaa cggcgtgaca   1800
cctggaacgt caaaagacct gaaggtcatc gcaggcccga ttagtgcgtc gttcactcct   1860
ttcgatcaca aggttgtgat ccataggggt ctcgtgtaca actacgactt ccccgaatac   1920
ggcgctatga aaccaggcgc cttcggagat atccaagcaa ccagcctgac ttctaaggac   1980
ctcatcgcga gcacagatat tcgtctgctc aaaccgtctg ctaagaacgt gcacgtcccc   2040
tacacccagg cctcttcagg tttcgagatg tggaaaaaca actccggcag gccgctccaa   2100
gaaaccgctc ctttcggctg caagatcgca gtcaaccct tgagagcggt tgactgtagc   2160
tacggaaaca tccccatttc tatcgatatt ccaaacgcag cgttcatccg cacatcagac   2220
gccccactcg ttagtacggt gaagtgcgag gtcagtgaat gtacatactc ggctgatttc   2280
ggtggtatgg ccacgttgca gtacgtttcg gaccgtgagg gtcaatgccc tgtgcactcc   2340
catagttcga ccgccactct gcaggagagc accgttcacg tgctcgaaaa gggtgctgtc   2400
accgttcatt tctcaactgc aagtcctcaa gcgaacttca tcgtgtctct ctgcggcaag   2460
aaaaccactt gcaacgcaga gtgtaagcca ccggcggacc acatcgtctc aacccccat   2520 aaaaacgatc aggagttcca agctgccatt tcgaagactt ccgaaaacct gtacttccag   2580
ggaggaggtg gaggatccgg tggaggaggt agcggaggag gtggatctgg tgctagggga   2640
ccagagtcca gattgctgga gttctacttg gctatgccct cgccaccc aatggaggct   2700 gaattggcaa gacgttccct ggcacaagac gcacctccac tgcctgtccc cggagttctc   2760
ttgaaggagt tcactgtgag cggtaacatc ttgaccatta ggctgactgc agcggaccac   2820
agacagttgc aactgtcaat ctccagctgc ctgcagcaac tcagtctgct catgtggatt   2880
acccagtgtt tcttgccagt tttcctcgct caacccccct cgggacagag aagacaccat   2940
catcatcatc at                                                      2952
```

<210> SEQ ID NO 3
<211> LENGTH: 449
<212> TYPE: PRT
<213> ORGANISM: Homo sapiens
<220> FEATURE:
<221> NAME/KEY: misc_feature
<223> OTHER INFORMATION: WT1 - Wilms tumor protein

<400> SEQUENCE: 3

```
Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65                  70                  75                  80
```

```
Ala Glu Pro His Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 4
<211> LENGTH: 1255
<212> TYPE: PRT
<213> ORGANISM: Homo sapiens
<220> FEATURE:
<221> NAME/KEY: misc_feature
<223> OTHER INFORMATION: Mucin-1 (MUC1)
```

```
<400> SEQUENCE: 4

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
                180                 185                 190

Pro Pro Ala His Gly Val Thr Ser Ala Pro Asp Thr Arg Pro Ala Pro
            195                 200                 205

Gly Ser Thr Ala Pro Pro Ala His Gly Val Thr Ser Ala Pro Asp Thr
210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
                260                 265                 270

Pro Pro Ala His Gly Val Thr Ser Ala Pro Asp Thr Arg Pro Ala Pro
            275                 280                 285

Gly Ser Thr Ala Pro Pro Ala His Gly Val Thr Ser Ala Pro Asp Thr
290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
                340                 345                 350

Pro Pro Ala His Gly Val Thr Ser Ala Pro Asp Thr Arg Pro Ala Pro
            355                 360                 365

Gly Ser Thr Ala Pro Pro Ala His Gly Val Thr Ser Ala Pro Asp Thr
370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
```

```
                405                 410                 415
Gly Val Thr Ser Ala Pro Asp Thr Arg Pro Ala Pro Gly Ser Thr Ala
            420                 425                 430
Pro Pro Ala His Gly Val Thr Ser Ala Pro Asp Thr Arg Pro Ala Pro
            435                 440                 445
Gly Ser Thr Ala Pro Pro Ala His Gly Val Thr Ser Ala Pro Asp Thr
        450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
                485                 490                 495
Gly Val Thr Ser Ala Pro Asp Thr Arg Pro Ala Pro Gly Ser Thr Ala
            500                 505                 510
Pro Pro Ala His Gly Val Thr Ser Ala Pro Asp Thr Arg Pro Ala Pro
            515                 520                 525
Gly Ser Thr Ala Pro Pro Ala His Gly Val Thr Ser Ala Pro Asp Thr
        530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
                565                 570                 575
Gly Val Thr Ser Ala Pro Asp Thr Arg Pro Ala Pro Gly Ser Thr Ala
            580                 585                 590
Pro Pro Ala His Gly Val Thr Ser Ala Pro Asp Thr Arg Pro Ala Pro
            595                 600                 605
Gly Ser Thr Ala Pro Pro Ala His Gly Val Thr Ser Ala Pro Asp Thr
        610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
                645                 650                 655
Gly Val Thr Ser Ala Pro Asp Thr Arg Pro Ala Pro Gly Ser Thr Ala
            660                 665                 670
Pro Pro Ala His Gly Val Thr Ser Ala Pro Asp Thr Arg Pro Ala Pro
            675                 680                 685
Gly Ser Thr Ala Pro Pro Ala His Gly Val Thr Ser Ala Pro Asp Thr
        690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
                725                 730                 735
Gly Val Thr Ser Ala Pro Asp Thr Arg Pro Ala Pro Gly Ser Thr Ala
            740                 745                 750
Pro Pro Ala His Gly Val Thr Ser Ala Pro Asp Thr Arg Pro Ala Pro
            755                 760                 765
Gly Ser Thr Ala Pro Pro Ala His Gly Val Thr Ser Ala Pro Asp Thr
        770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
                805                 810                 815
Gly Val Thr Ser Ala Pro Asp Thr Arg Pro Ala Pro Gly Ser Thr Ala
            820                 825                 830
```

Pro Pro Ala His Gly Val Thr Ser Ala Pro Asp Thr Arg Pro Ala Pro
                835                 840                 845

Gly Ser Thr Ala Pro Pro Ala His Gly Val Thr Ser Ala Pro Asp Thr
        850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
                915                 920                 925

Gly Ser Thr Ala Pro Pro Ala His Gly Val Thr Ser Ala Pro Asp Asn
        930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Ser Thr His His Ser Ser Val Pro
        1010                1015                1020

Pro Leu Thr Ser Ser Asn His Ser Thr Ser Pro Gln Leu Ser Thr
    1025                1030                1035

Gly Val Ser Phe Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Thr Ser Ala Asn Leu
    1250            1255

<210> SEQ ID NO 5
<211> LENGTH: 497
<212> TYPE: PRT
<213> ORGANISM: Homo sapiens
<220> FEATURE:
<221> NAME/KEY: misc_feature
<223> OTHER INFORMATION: Latent membrane protein 2 (LMP2)

<400> SEQUENCE: 5

Met Gly Ser Leu Glu Met Val Pro Met Gly Ala Gly Pro Pro Ser Pro
1               5                   10                  15

Gly Gly Asp Pro Asp Gly Tyr Asp Gly Gly Asn Asn Ser Gln Tyr Pro
            20                  25                  30

Ser Ala Ser Gly Ser Ser Gly Asn Thr Pro Thr Pro Pro Asn Asp Glu
        35                  40                  45

Glu Arg Glu Ser Asn Glu Glu Pro Pro Pro Tyr Glu Asp Pro Tyr
    50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95

Pro Pro Pro Pro Tyr Ser Pro Arg Asp Asp Ser Ser Gln His Ile Tyr
            100                 105                 110

Glu Glu Ala Gly Arg Gly Ser Met Asn Pro Val Cys Leu Pro Val Ile
        115                 120                 125

Val Ala Pro Tyr Leu Phe Trp Leu Ala Ala Ile Ala Ala Ser Cys Phe
    130                 135                 140

Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
                165                 170                 175

Lys Leu Leu Thr Pro Val Thr Val Leu Thr Ala Val Val Thr Phe Phe
            180                 185                 190

Ala Ile Cys Leu Thr Trp Arg Ile Glu Asp Pro Pro Phe Asn Ser Leu
        195                 200                 205

Leu Phe Ala Leu Leu Ala Ala Ala Gly Gly Leu Gln Gly Ile Tyr Val
    210                 215                 220

Leu Val Met Leu Val Leu Leu Ile Leu Ala Tyr Arg Arg Arg Trp Arg
225                 230                 235                 240

Arg Leu Thr Val Cys Gly Gly Ile Met Phe Leu Ala Cys Val Leu Val
                245                 250                 255

Leu Ile Val Asp Ala Val Leu Gln Leu Ser Pro Leu Leu Gly Ala Val
            260                 265                 270

Thr Val Val Ser Met Thr Leu Leu Leu Leu Ala Phe Val Leu Trp Leu
        275                 280                 285

Ser Ser Pro Gly Gly Leu Gly Thr Leu Gly Ala Ala Leu Leu Thr Leu
    290                 295                 300

Ala Ala Ala Leu Ala Leu Leu Ala Ser Leu Ile Leu Gly Thr Leu Asn
305                 310                 315                 320

Leu Thr Thr Met Phe Leu Leu Met Leu Leu Trp Thr Leu Val Val Leu
                325                 330                 335

```
Leu Ile Cys Ser Ser Cys Ser Ser Cys Pro Leu Ser Lys Ile Leu Leu
                340                 345                 350

Ala Arg Leu Phe Leu Tyr Ala Leu Ala Leu Leu Leu Ala Ser Ala
            355                 360                 365

Leu Ile Ala Gly Gly Ser Ile Leu Gln Thr Asn Phe Lys Ser Leu Ser
370                 375                 380

Ser Thr Glu Phe Ile Pro Asn Leu Phe Cys Met Leu Leu Ile Val
385                 390                 395                 400

Ala Gly Ile Leu Phe Ile Leu Ala Ile Leu Thr Glu Trp Gly Ser Gly
                405                 410                 415

Asn Arg Thr Tyr Gly Pro Val Phe Met Cys Leu Gly Gly Leu Leu Thr
            420                 425                 430

Met Val Ala Gly Ala Val Trp Leu Thr Val Met Ser Asn Thr Leu Leu
            435                 440                 445

Ser Ala Trp Ile Leu Thr Ala Gly Phe Leu Ile Phe Leu Ile Gly Phe
            450                 455                 460

Ala Leu Phe Gly Val Ile Arg Cys Cys Arg Tyr Cys Cys Tyr Tyr Cys
465                 470                 475                 480

Leu Thr Leu Glu Ser Glu Glu Arg Pro Pro Thr Pro Tyr Arg Asn Thr
                485                 490                 495

Val

<210> SEQ ID NO 6
<211> LENGTH: 158
<212> TYPE: PRT
<213> ORGANISM: Human papillomavirus type 16
<220> FEATURE:
<221> NAME/KEY: misc_feature
<223> OTHER INFORMATION: Protein E6

<400> SEQUENCE: 6

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 7
<211> LENGTH: 98
<212> TYPE: PRT
<213> ORGANISM: Human papillomavirus type 16
```

```
<220> FEATURE:
<221> NAME/KEY: misc_feature
<223> OTHER INFORMATION: Protein E7

<400> SEQUENCE: 7

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 8
<211> LENGTH: 150
<212> TYPE: PRT
<213> ORGANISM: Human papillomavirus type 18
<220> FEATURE:
<221> NAME/KEY: misc_feature
<223> OTHER INFORMATION: Protein E6

<400> SEQUENCE: 8

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
            115                 120                 125

Asn Ile Ala Gly His Tyr Arg Gly Gln Cys His Ser Cys Cys Asn Arg
        130                 135                 140

Ala Arg Gln Glu Arg Leu
145                 150

<210> SEQ ID NO 9
<211> LENGTH: 105
<212> TYPE: PRT
<213> ORGANISM: Human papillomavirus type 18
<220> FEATURE:
<221> NAME/KEY: misc_feature
<223> OTHER INFORMATION: Protein E7

<400> SEQUENCE: 9

Met His Gly Pro Lys Ala Thr Leu Gln Asp Ile Val Leu His Leu Glu
```

```
                 1               5                  10                 15
Pro Gln Asn Glu Ile Pro Val Asp Leu Leu Cys His Glu Gln Leu Ser
                20                  25                 30

Asp Ser Glu Glu Glu Asn Asp Glu Ile Asp Gly Val Asn His Gln His
                35                  40                 45

Leu Pro Ala Arg Arg Ala Glu Pro Gln Arg His Thr Met Leu Cys Met
                50                  55                 60

Cys Cys Lys Cys Glu Ala Arg Ile Lys Leu Val Val Glu Ser Ser Ala
 65                 70                  75                 80

Asp Asp Leu Arg Ala Phe Gln Gln Leu Phe Leu Asn Thr Leu Ser Phe
                85                  90                 95

Val Cys Pro Trp Cys Ala Ser Gln Gln
                100                 105

<210> SEQ ID NO 10
<211> LENGTH: 473
<212> TYPE: PRT
<213> ORGANISM: Homo sapiens
<220> FEATURE:
<221> NAME/KEY: misc_feature
<223> OTHER INFORMATION: Ral-GDS-related protein (RGL4)

<400> SEQUENCE: 10

Met Arg Lys Leu Leu Thr Asn Leu Pro Ala Ala Val Leu Ser Ala
 1               5                  10                 15

Gln Val Tyr Ser Ala Val Leu Gln Gly Leu Trp Glu Glu Asn Val Cys
                20                  25                 30

Gly Thr Pro Gly Arg Thr Arg Val Cys Thr Ala Leu Leu Tyr Gly Gln
                35                  40                 45

Val Cys Pro Phe Gln Asp Ser Thr Asp Gly Leu Arg Thr Ile Thr Ser
                50                  55                 60

Ile Leu Phe Asn Trp Pro Pro Glu Asn Thr Ser Val Tyr Tyr Gln Pro
 65                 70                  75                 80

Pro Gln Arg Ser Ser Phe Arg Ile Lys Leu Ala Phe Arg Asn Leu Ser
                85                  90                 95

Trp Pro Gly Leu Gly Leu Glu Asp His Gln Glu Ile Val Leu Gly Gln
                100                 105                110

Leu Val Leu Pro Glu Pro Asn Glu Ala Lys Pro Asp Asp Pro Ala Pro
                115                 120                125

Arg Pro Gly Gln His Ala Leu Thr Met Pro Ala Leu Glu Pro Ala Pro
                130                 135                140

Pro Leu Leu Ala Asp Leu Gly Pro Ala Leu Glu Pro Glu Ser Pro Ala
145                 150                 155                160

Ala Leu Gly Pro Pro Gly Tyr Leu His Ser Ala Pro Gly Pro Ala Pro
                165                 170                175

Ala Pro Gly Glu Gly Pro Pro Pro Gly Thr Val Leu Glu Pro Gln Ser
                180                 185                190

Ala Pro Glu Ser Ser Cys Pro Cys Arg Gly Ser Val Lys Asn Gln Pro
                195                 200                205

Ser Glu Glu Leu Pro Asp Met Thr Thr Phe Pro Pro Arg Leu Leu Ala
                210                 215                220

Glu Gln Leu Thr Leu Met Asp Ala Glu Leu Phe Lys Lys Val Val Leu
225                 230                 235                240

His Glu Cys Leu Gly Cys Ile Trp Gly Gln Gly His Leu Lys Gly Asn
                245                 250                255
```

```
Glu His Met Ala Pro Thr Val Arg Ala Thr Ile Ala His Phe Asn Arg
                260                 265                 270

Leu Thr Asn Cys Ile Thr Thr Ser Cys Leu Gly Asp His Ser Met Arg
            275                 280                 285

Ala Arg Asp Arg Ala Arg Val Val Glu His Trp Ile Lys Val Ala Arg
        290                 295                 300

Glu Cys Leu Ser Leu Asn Asn Phe Ser Ser Val His Val Ile Val Ser
305                 310                 315                 320

Ala Leu Cys Ser Asn Pro Ile Gly Gln Leu His Lys Thr Trp Ala Gly
                325                 330                 335

Val Ser Ser Lys Ser Met Lys Glu Leu Lys Glu Leu Cys Lys Lys Asp
            340                 345                 350

Thr Ala Val Lys Arg Asp Leu Leu Ile Lys Ala Gly Ser Phe Lys Val
        355                 360                 365

Ala Thr Gln Glu Arg Asn Pro Gln Arg Val Gln Met Arg Leu Arg Arg
    370                 375                 380

Gln Lys Lys Gly Val Val Pro Phe Leu Gly Asp Phe Leu Thr Glu Leu
385                 390                 395                 400

Gln Arg Leu Asp Ser Ala Ile Pro Asp Asp Leu Asp Gly Asn Thr Asn
                405                 410                 415

Lys Arg Ser Lys Glu Val Arg Val Leu Gln Glu Met Gln Leu Leu Gln
            420                 425                 430

Val Ala Ala Met Asn Tyr Arg Leu Arg Pro Leu Glu Lys Phe Val Thr
        435                 440                 445

Tyr Phe Thr Arg Met Gln Leu Ser Asp Lys Glu Ser Tyr Lys Leu
    450                 455                 460

Ser Cys Gln Leu Glu Pro Glu Asn Pro
465                 470

<210> SEQ ID NO 11
<211> LENGTH: 180
<212> TYPE: PRT
<213> ORGANISM: Homo sapiens
<220> FEATURE:
<221> NAME/KEY: misc_feature
<223> OTHER INFORMATION: Cancer/testis antigen 1 (NY-ESO-1)

<400> SEQUENCE: 11

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Gly Ala Pro Arg Gly Pro
        50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140
```

```
Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 12
<211> LENGTH: 1245
<212> TYPE: PRT
<213> ORGANISM: Sindbis virus
<220> FEATURE:
<221> NAME/KEY: misc_feature
<223> OTHER INFORMATION: Full Sindbis structural protein sequence
      (Capsid, E3, E2 Ectodomain, E2 Transmembrane Domain, 6K, E1
      Ectodomain, E1 Transmembrane Domain)

<400> SEQUENCE: 12

Met Asn Arg Gly Phe Phe Asn Met Leu Gly Arg Arg Pro Phe Pro Ala
1               5                   10                  15

Pro Thr Ala Met Trp Arg Pro Arg Arg Arg Gln Ala Ala Pro Met
            20                  25                  30

Pro Ala Arg Asn Gly Leu Ala Ser Gln Ile Gln Gln Leu Thr Thr Ala
            35                  40                  45

Val Ser Ala Leu Val Ile Gly Gln Ala Thr Arg Pro Gln Pro Pro Arg
50                  55                  60

Pro Arg Pro Pro Arg Gln Lys Lys Gln Ala Pro Lys Gln Pro
65                  70                  75                  80

Lys Pro Lys Lys Pro Lys Thr Gln Glu Lys Lys Lys Gln Pro Ala
                85                  90                  95

Lys Pro Lys Pro Gly Lys Arg Gln Arg Met Ala Leu Lys Leu Glu Ala
            100                 105                 110

Asp Arg Leu Phe Asp Val Lys Asn Glu Asp Gly Asp Val Ile Gly His
            115                 120                 125

Ala Leu Ala Met Glu Gly Lys Val Met Lys Pro Leu His Val Lys Gly
130                 135                 140

Thr Ile Asp His Pro Val Leu Ser Lys Leu Lys Phe Thr Lys Ser Ser
145                 150                 155                 160

Ala Tyr Asp Met Glu Phe Ala Gln Leu Pro Val Asn Met Arg Ser Glu
                165                 170                 175

Ala Phe Thr Tyr Thr Ser Glu His Pro Glu Gly Phe Tyr Asn Trp His
            180                 185                 190

His Gly Ala Val Gln Tyr Ser Gly Gly Arg Phe Thr Ile Pro Arg Gly
            195                 200                 205

Val Gly Gly Arg Gly Asp Ser Gly Arg Pro Ile Met Asp Asn Ser Gly
        210                 215                 220

Arg Val Val Ala Ile Val Leu Gly Gly Ala Asp Glu Gly Thr Arg Thr
225                 230                 235                 240

Ala Leu Ser Val Val Thr Trp Asn Ser Lys Gly Lys Thr Ile Lys Thr
                245                 250                 255

Thr Pro Glu Gly Thr Glu Glu Trp Ser Ala Ala Pro Leu Val Thr Ala
            260                 265                 270

Met Cys Leu Leu Gly Asn Val Ser Phe Pro Cys Asp Arg Pro Pro Thr
            275                 280                 285

Cys Tyr Thr Arg Glu Pro Ser Arg Ala Leu Asp Ile Leu Glu Glu Asn
        290                 295                 300
```

```
Val Asn His Glu Ala Tyr Asp Thr Leu Leu Asn Ala Ile Leu Arg Cys
305                 310                 315                 320

Gly Ser Ser Gly Arg Ser Lys Arg Ser Val Ile Asp Asp Phe Thr Leu
            325                 330                 335

Thr Ser Pro Tyr Leu Gly Thr Cys Ser Tyr Cys His His Thr Val Pro
        340                 345                 350

Cys Phe Ser Pro Val Lys Ile Glu Gln Val Trp Asp Glu Ala Asp Asp
    355                 360                 365

Asn Thr Ile Arg Ile Gln Thr Ser Ala Gln Phe Gly Tyr Asp Gln Ser
370                 375                 380

Gly Ala Ser Ala Asn Lys Tyr Arg Tyr Met Ser Leu Lys Gln Asp
385                 390                 395                 400

His Thr Val Lys Glu Gly Thr Met Asp Asp Ile Lys Ile Ser Thr Ser
                405                 410                 415

Gly Pro Cys Arg Arg Leu Ser Tyr Lys Gly Tyr Phe Leu Leu Ala Lys
            420                 425                 430

Cys Pro Pro Gly Asp Ser Val Thr Val Ser Ile Val Ser Ser Asn Ser
        435                 440                 445

Ala Thr Ser Cys Thr Leu Ala Arg Lys Ile Lys Pro Lys Phe Val Gly
450                 455                 460

Arg Glu Lys Tyr Asp Leu Pro Pro Val His Gly Lys Lys Ile Pro Cys
465                 470                 475                 480

Thr Val Tyr Asp Arg Leu Lys Glu Thr Thr Ala Gly Tyr Ile Thr Met
                485                 490                 495

His Arg Pro Arg Pro His Ala Tyr Thr Ser Tyr Leu Glu Glu Ser Ser
            500                 505                 510

Gly Lys Val Tyr Ala Lys Pro Pro Ser Gly Lys Asn Ile Thr Tyr Glu
        515                 520                 525

Cys Lys Cys Gly Asp Tyr Lys Thr Gly Thr Val Ser Thr Arg Thr Glu
    530                 535                 540

Ile Thr Gly Cys Thr Ala Ile Lys Gln Cys Val Ala Tyr Lys Ser Asp
545                 550                 555                 560

Gln Thr Lys Trp Val Phe Asn Ser Pro Asp Leu Ile Arg His Asp Asp
                565                 570                 575

His Thr Ala Gln Gly Lys Leu His Leu Pro Phe Lys Leu Ile Pro Ser
            580                 585                 590

Thr Cys Met Val Pro Val Ala His Ala Pro Asn Val Ile His Gly Phe
        595                 600                 605

Lys His Ile Ser Leu Gln Leu Asp Thr Asp His Leu Thr Leu Leu Thr
    610                 615                 620

Thr Arg Arg Leu Gly Ala Asn Pro Glu Pro Thr Thr Glu Trp Ile Val
625                 630                 635                 640

Gly Lys Thr Val Arg Asn Phe Thr Val Asp Arg Asp Gly Leu Glu Tyr
                645                 650                 655

Ile Trp Gly Asn His Glu Pro Val Arg Val Tyr Ala Gln Glu Ser Ala
            660                 665                 670

Pro Gly Asp Pro His Gly Trp Pro His Glu Ile Val Gln His Tyr Tyr
        675                 680                 685

His Arg His Pro Val Tyr Thr Ile Leu Ala Val Ala Ser Ala Thr Val
    690                 695                 700

Ala Met Met Ile Gly Val Thr Val Ala Val Leu Cys Ala Cys Lys Ala
705                 710                 715                 720
```

```
Arg Arg Glu Cys Leu Thr Pro Tyr Ala Leu Ala Pro Asn Ala Val Ile
            725                 730                 735

Pro Thr Ser Leu Ala Leu Leu Cys Cys Val Arg Ser Ala Asn Ala Glu
            740                 745                 750

Thr Phe Thr Glu Thr Met Ser Tyr Leu Trp Ser Asn Ser Gln Pro Phe
            755                 760                 765

Phe Trp Val Gln Leu Cys Ile Pro Leu Ala Ala Phe Ile Val Leu Met
            770                 775                 780

Arg Cys Cys Ser Cys Cys Leu Pro Phe Leu Val Ala Gly Ala Tyr
785                 790                 795                 800

Leu Ala Lys Val Asp Ala Tyr Glu His Ala Thr Thr Val Pro Asn Val
                805                 810                 815

Pro Gln Ile Pro Tyr Lys Ala Leu Val Glu Arg Ala Gly Tyr Ala Pro
            820                 825                 830

Leu Asn Leu Glu Ile Thr Val Met Ser Ser Glu Val Leu Pro Ser Thr
            835                 840                 845

Asn Gln Glu Tyr Ile Thr Cys Lys Phe Thr Thr Val Val Pro Ser Pro
            850                 855                 860

Lys Ile Lys Cys Cys Gly Ser Leu Glu Cys Gln Pro Ala Ala His Ala
865                 870                 875                 880

Asp Tyr Thr Cys Lys Val Phe Gly Gly Val Tyr Pro Phe Met Trp Gly
                885                 890                 895

Gly Ala Gln Cys Phe Cys Asp Ser Glu Asn Ser Gln Met Ser Glu Ala
            900                 905                 910

Tyr Val Glu Leu Ser Ala Asp Cys Ala Ser Asp His Ala Gln Ala Ile
            915                 920                 925

Lys Val His Thr Ala Ala Met Lys Val Gly Leu Arg Ile Val Tyr Gly
            930                 935                 940

Asn Thr Thr Ser Phe Leu Asp Val Tyr Val Asn Gly Val Thr Pro Gly
945                 950                 955                 960

Thr Ser Lys Asp Leu Lys Val Ile Ala Gly Pro Ile Ser Ala Ser Phe
                965                 970                 975

Thr Pro Phe Asp His Lys Val Val Ile His Arg Gly Leu Val Tyr Asn
            980                 985                 990

Tyr Asp Phe Pro Glu Tyr Gly Ala Met Lys Pro Gly Ala Phe Gly Asp
            995                 1000                1005

Ile Gln Ala Thr Ser Leu Thr Ser Lys Asp Leu Ile Ala Ser Thr
            1010            1015            1020

Asp Ile Arg Leu Leu Lys Pro Ser Ala Lys Asn Val His Val Pro
            1025            1030            1035

Tyr Thr Gln Ala Ser Ser Gly Phe Glu Met Trp Lys Asn Asn Ser
            1040            1045            1050

Gly Arg Pro Leu Gln Glu Thr Ala Pro Phe Gly Cys Lys Ile Ala
            1055            1060            1065

Val Asn Pro Leu Arg Ala Val Asp Cys Ser Tyr Gly Asn Ile Pro
            1070            1075            1080

Ile Ser Ile Asp Ile Pro Asn Ala Ala Phe Ile Arg Thr Ser Asp
            1085            1090            1095

Ala Pro Leu Val Ser Thr Val Lys Cys Glu Val Ser Glu Cys Thr
            1100            1105            1110

Tyr Ser Ala Asp Phe Gly Gly Met Ala Thr Leu Gln Tyr Val Ser
            1115            1120            1125

Asp Arg Glu Gly Gln Cys Pro Val His Ser His Ser Ser Thr Ala
```

```
             1130                1135                1140
Thr Leu Gln Glu Ser Thr Val His Val Leu Glu Lys Gly Ala Val
        1145                1150                1155

Thr Val His Phe Ser Thr Ala Ser Pro Gln Ala Asn Phe Ile Val
    1160                1165                1170

Ser Leu Cys Gly Lys Lys Thr Thr Cys Asn Ala Glu Cys Lys Pro
        1175                1180                1185

Pro Ala Asp His Ile Val Ser Thr Pro His Lys Asn Asp Gln Glu
    1190                1195                1200

Phe Gln Ala Ala Ile Ser Lys Thr Ser Trp Ser Trp Leu Phe Ala
    1205                1210                1215

Leu Phe Gly Gly Ala Ser Ser Leu Leu Ile Ile Gly Leu Met Ile
    1220                1225                1230

Phe Ala Cys Ser Met Met Leu Thr Ser Thr Arg Arg
    1235                1240                1245

<210> SEQ ID NO 13
<211> LENGTH: 19
<212> TYPE: PRT
<213> ORGANISM: Artificial Sequence
<220> FEATURE:
<223> OTHER INFORMATION: Synthetic: glycine/serine linker

<400> SEQUENCE: 13

Gly Gly Gly Gly Ser Gly Gly Gly Gly Ser Gly Gly Gly Gly Ser Gly
1               5                   10                  15

Gly Gly Gly

<210> SEQ ID NO 14
<211> LENGTH: 6
<212> TYPE: PRT
<213> ORGANISM: Artificial Sequence
<220> FEATURE:
<223> OTHER INFORMATION: Synthetic: TEV cleavage site

<400> SEQUENCE: 14

Glu Asn Leu Tyr Phe Gln
1               5

<210> SEQ ID NO 15
<211> LENGTH: 16
<212> TYPE: PRT
<213> ORGANISM: Artificial Sequence
<220> FEATURE:
<223> OTHER INFORMATION: Synthetic: glycine/serine Linker

<400> SEQUENCE: 15

Gly Gly Gly Gly Gly Ser Gly Gly Gly Gly Ser Gly Gly Gly Gly Ser
1               5                   10                  15
```